United States Patent
Awasthi et al.

(10) Patent No.: US 10,022,403 B2
(45) Date of Patent: Jul. 17, 2018

(54) METHODS, COMPOSITIONS, AND KITS FOR IMPROVING PANCREATIC BETA CELL VIABILITY AND TREATING DISEASES OR CONDITIONS RELATED TO BETA CELL DESTRUCTION

(71) Applicant: CITY OF HOPE, Duarte, CA (US)

(72) Inventors: Sanjay Awasthi, San Marino, CA (US); Sushma Yadav, Duarte, CA (US); Ismail Al Abdullah, Duarte, CA (US); Fouad Kandeel, Duarte, CA (US); Brian McFadden, Duarte, CA (US); Indu Nair, Duarte, CA (US); Sharad S. Singhal, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/659,568

(22) Filed: Mar. 16, 2015

(65) Prior Publication Data

US 2016/0151423 A1 Jun. 2, 2016

Related U.S. Application Data

(60) Provisional application No. 61/953,725, filed on Mar. 14, 2014.

(51) Int. Cl.
*A61K 35/39* (2015.01)
*C12N 5/071* (2010.01)
*A61K 38/45* (2006.01)
*C12N 9/10* (2006.01)

(52) U.S. Cl.
CPC .............. *A61K 35/39* (2013.01); *A61K 38/45* (2013.01); *C12N 5/0676* (2013.01); *C12N 9/1088* (2013.01); *C12Y 205/01018* (2013.01); *C12N 2501/72* (2013.01)

(58) Field of Classification Search
CPC .... C12N 5/0676; C12N 9/1088; C12N 15/86; C12N 2501/72; A61K 38/465; A61K 38/45; A61K 35/39; C12Y 205/01018
See application file for complete search history.

(56) References Cited

PUBLICATIONS

Yang et al 2008, Toxicology and Applied Pharmacology 230:187-196.*
Cheng et al 2001 Arch. Biochem. Biophys. 392:197-207.*
Chou et al 2009, J. Biomed. Sci. 16:71 pp. 1-10.*
Awasthi et al 2003, Molecular Aspects of Medicine 24:219-230.*
Craig et al (2009, Virology Journal 6:6, pp. 1-10.*
Wilma et al 1996, Endocrinology 137:5290-5296.*
Awasthi, S., et al., "RLIP76 Is a Major Determinant of Radiation Sensitivity" Cancer Research 65: 6022-6028 (2005).
Awasthi, S., et al., "A Central Role of RLIP76 in Regulation of Glycemic Control" Diabetes 59(3): 714-725 (2010).
Awasthi, Y., et al., "Human Glutathione S-Transferasas" Int. J. Biochem. 26: 295-308 (1994).
Engle, M., et al., "Physiological Role of mGSTA-4-4, a Glutathione S-Transferase Metabolizing 4-Hydroxynonenal: Generation and Analysis of mGsta4 Null Mouse" Toxicology and Applied Pharmacology 194: 296-308 (2004).
Jakoby, W., "The Glutathione S-Transferases: A Group of Multi-functional Detoxification Proteins" Adv. Enzymol Relat. Areas Mol. Biol. 46: 383-414 (1978).
Papadakis, E.D., et al., "Promoters and Control Elements: Designing Expression Cassettes for Gene Therapy" Current Gene Therapy 4: 89-113 (2005).
Sharma, R., et al., "Antioxidant Role of Glutathione S-Transferases: Protection Against Oxidant Toxicity and Regulation of Stress-Mediated Apoptosis" Antioxidants & Redox Signaling 6(2): 289-300 (2004).
Singhal, J., et al., "RLIP76, a Glutathione-Conjugate Transporter, Plays a Major Role in the Pathogenesis of Metabolic Syndrome" PLos ONE 6(9): e24688 (2011).
Singhal, S., et al., "Glutathione-Conjugate transport by RLIP76 in Required for Clathrin-Dependent endocytosis and Chemical Carcinogenesis" Mol. Cancer Ther. 10(1): 16-28 (2011).
Singhal, S., et al., "RLIP76 Protein knockdown attenuates obesity due to a High-fat diet" J. Bio. Chem. 288(32): 233940-23406 (2013).
Warnke, M., et al., "The determination of glutathione-4-hydroxynonenal (GSHNE), E-4-hydroxynonenal (HNE), and E-1-hydroxynon-2-en-4-one (HNO) in mouse liver tissue by LC-ESI-MS" Analyt. Bioanal. Chem. 392: 1325-1333 (2008).
Yang, Y. et al., "Role of alpha class glutathione S-Transferases as antioxidants enzymes in rodent tissues" Toxicology and Applied Pharmacology 182: 105-115 (2002).

\* cited by examiner

*Primary Examiner* — Christopher M Babic
*Assistant Examiner* — Kelaginamane Hiriyanna
(74) *Attorney, Agent, or Firm* — Perkins Coie LLP

(57) ABSTRACT

The present disclosure provides novel methods for increasing β-cell viability in islets by delivering RLIP76 polypeptides or GSTA4 polypeptides, or a combination thereof; or RLIP76 polynucleotides or GSTA4 polynucleotides, or a combination thereof, to the islets. The disclosure also provides novel methods for treating a disease or condition in a subject, such as type 1 diabetes mellitus, by delivering RLIP76 polypeptides or GSTA4 polypeptides, or a combination thereof; or RLIP76 polynucleotides or GSTA4 polynucleotides, or a combination thereof, to islets and transplanting the islets into the subject to treat the disease or condition. Kits and compositions including RLIP76 polypeptides or GSTA4 polypeptides, or a combination thereof; or RLIP76 polynucleotides or GSTA4 polynucleotides, or a combination thereof, are also provided to increase β-cell viability.

7 Claims, 23 Drawing Sheets

Fig. 6A
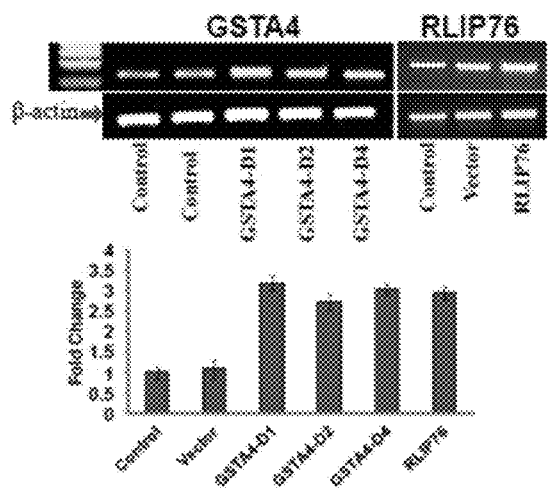
Fig. 6B
Fig. 6D
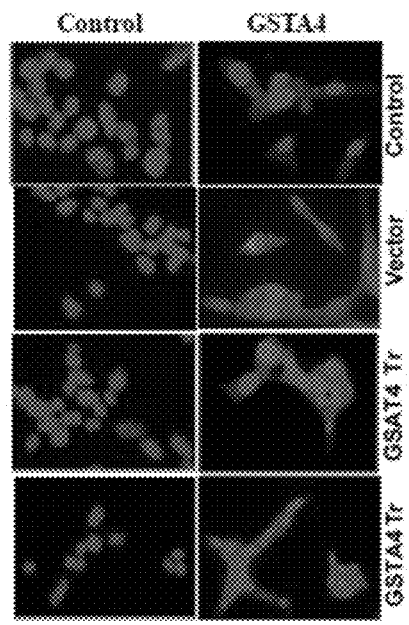
Fig. 6C
| Primer Name | RT-PCR Primers | SEQ ID: NO |
|---|---|---|
| GSTA4 Forward | CAGGAGTCATGGAAGTCAAAC | SEQ ID NO: 6 |
| GSTA4 Reverse | TTCTCATATTGTTCTCTCGTCTC | SEQ ID NO: 7 |
| RLIP76 Forward | TTCAAGAAGCCCAGCTTTTC | SEQ ID NO: 8 |
| RLIP76 Reverse | ATTCTCTGGAAGGTCTCGCA | SEQ ID NO: 9 |
| β-actin Forward | CACCCGCGACTACAACCTTC | SEQ ID NO: 10 |
| β-actin Reverse | CCCATACCCACCATCACACC | SEQ ID NO: 11 |

FIG. 16

RLIP76 DNA sequence (SEQ ID NO: 1):

ATGACTGAGTGCTTCCTGCCCCCCACCAGCAGCCCCAGTGAACACCGCAGGGTG
GAGCATGGCAGCGGGCTTACCCGGACCCCCAGCTCTGAAGAGATCAGCCCTACTA
AGTTTCCTGGATTGTACCGCACTGGCGAGCCCTCACCTCCCCATGACATCCTCCAT
GAGCCTCCTGATGTAGTGTCTGATGATGAGAAAGATCATGGGAAGAAAAAGGGA
AATTTAAGAAAAAGGAAAAGAGGACTGAAGGCTATGCAGCCTTTCAGGAAGATAGC
TCTGGAGATGAGGCAGAAAGTCCTTCTAAAATGAAGAGGTCCAAGGGAATCCATGT
TTTCAAGAAGCCCAGCTTTTCTAAAAAGAAGGAAAAGGATTTTAAAATAAAAGAGAA
ACCCAAAGAAGAAAAGCATAAAGAAGAAAAGCACAAAGAAGAAAAACATAAAGAGA
AGAAGTCAAAAGACTTGACAGCAGCTGATGTTGTTAAACAGTGGAAGGAAAAGAAG
AAAAAGAAAAAGCCAATTCAGGAGCCAGAGGTGCCTCAGATTGATGTTCCAAATCT
CAAACCCATTTTTGGAATTCCTTTGGCTGATGCAGTAGAGAGGACCATGATGTATG
ATGGCATTCGGCTGCCAGCCGTTTTCCGTGAATGTATAGATTACGTAGAGAAGTAT
GGCATGAAGTGTGAAGGCATCTACAGAGTATCAGGAATTAAATCAAAGGTGGATGA
GCTAAAAGCAGCCTATGACCGGGAGGAGTCTACAAACTTGGAAGACTATGAGCCT
AACACTGTAGCCAGTTTGCTGAAGCAGTATTTGCGAGACCTTCCAGAGAATTTGCT
TACCAAAGAGCTTATGCCCAGATTTGAAGAGGCTTGTGGAGGACCACGGAGACT
GAGAAAGTGCAGGAATTCCAGCGTTTACTCAAAGAACTGCCAGAATGTAACTATCT
TCTGATTTCTTGGCTCATTGTGCACATGGACCATGTCATTGCAAAGGAACTGGAAA
CAAAAATGAATATACAGAACATTTCTATAGTGCTCAGCCCAACTGTGCAGATCAGC
AATCGAGTCCTGTATGTGTTTTTCACACATGTGCAAGAACTCTTTGGAAATGTGGTA
CTAAAGCAAGTGATGAAACCTCTGCGATGGTCTAACATGGCCACGATGCCCACGC
TGCCAGAGACCCAGGCGGGCATCAAGGAGGAGATCAGGAGACAGGAGTTTCTTTT
GAATTGTTTACATCGAGATCTGCAGGGTGGGATAAAGGATTTGTCTAAAGAAGAAA
GATTATGGGAAGTACAAAGAATTTTGACAGCCCTCAAAAGAAAACTGAGAGAAGCT
AAAAGACAGGAGTGTGAAACCAAGATTGCACAAGAGATAGCCAGTCTTTCAAAAGA
GGATGTTTCCAAAGAAGAGATGAATGAAAATGAAGAAGTTATAAATATTCTCCTTGC
TCAGGAGAATGAGATCCTGACTGAACAGGAGGAGCTCCTGGCCATGGAGCAGTTT
CTGCGCCGGCAGATTGCCTCAGAAAAGAAGAGATTGAACGCCTCAGAGCTGAGA
TTGCTGAAATTCAGAGTCGCCAGCAGCACGGCCGAAGTGAGACTGAGGAGTACTC
CTCCGAGAGCGAGAGCGAGAGTGAGGATGAGGAGGAGCTGCAGATCATTCTGGA
AGACTTACAGAGACAGAACGAAGAGCTGGAAATAAAGAACAATCATTTGAATCAAG
CAATTCATGAGGAGCGCGAGGCCATCATCGAGCTGCGCGTGCAGCTGCGGCTGC
TCCAGATGCAGCGAGCCAAGGCCGAGCAGCAGGCGCAGGAGGACGAGGAGCCT
GAGTGGCGCGGGGGTGCCGTCCAGCCGCCCAGAGACGGCGTCCTTGAGCCAAAA
GCAGCTAAAGAGCAGCCAAAGGCAGGCAAGGAGCCGGCAAAGCCATCGCCCAGC
AGGGATAGGAAGGAGACGTCCATCTGA

FIG. 16 continued

RLIP76 amino acid sequence (SEQ ID NO: 2)

MTECFLPPTSSPSEHRRVEHGSGLTRTPSSEEISPTKFPGLYRTGEPSPPHDILHEPPD
VVSDDEKDHGKKKGKFKKKEKRTEGYAAFQEDSSGDEAESPSKMKRSKGIHVFKKPS
FSKKKEKDFKIKEKPKEEKHKEEKHHKEEKHKEKKSKDLTAADVVKQWKEKKKKKKPIQ
EPEVPQIDVPNLKPIFGIPLADAVERTMMYDGIRLPAVFRECIDYVEKYGMKCEGIYRVS
GIKSKVDELKAAYDREESTNLEDYEPNTVASLLKQYLRDLPENLLTKELMPRFEEACGR
TTETEKVQEFQRLLKELPECNYLLISWLIVHMDHVIAKELETKMNIQNISIVLSPTVQISN
RVLYVFFTHVQELFGNVVLKQVMKPLRWSNMATMPTLPETQAGIKEEIRRQEFLLNCL
HRDLQGGIKDLSKEERLWEVQRILTALKRKLREAKRQECETKIAQEIASLSKEDVSKEE
MNENEEVINILLAQENEILTEQEELLAMEQFLRRQIASEKEEIERLRAEIAEIQSRQQHGR
SETEEYSSESESESEDEEELQIILEDLQRQNEELEIKNNHLNQAIHEEREAIIELRVQLRL
LQMQRAKAEQQAQEDEEPEWRGGAVQPPRDGVLEPKAAKEQPKAGKEPAKPSPSR
DRKETSI

FIG. 17

GSTA4 DNA sequence (SEQ ID NO: 3):

ATGGCAGCAAGGCCCAAGCTCCACTATCCCAACGGAAGAGGCCGGATGGAGTCC
GTGAGATGGGTTTTAGCTGCCGCCGGAGTCGAGTTTGATGAAGAATTTCTGGAAA
CAAAAGAACAGTTGTACAAGTTGCAGGATGGTAACCACCTGCTGTTCCAACAAGTG
CCCATGGTTGAAATTGACGGGATGAAGTTGGTACAGACCCGAAGCATTCTCCACTA
CATAGCAGACAAGCACAATCTCTTTGGCAAGAACCTCAAGGAGAGAACCCTGATTG
ACATGTACGTGGAGGGGACACTGGATCTGCTGGAACTGCTTATCATGCATCCTTTC
TTAAAACCAGATGATCAGCAAAAGGAAGTGGTTAACATGGCCCAGAAGGCTATAAT
TAGATACTTTCCTGTGTTTGAAAAGATTTTAAGGGGTCACGGACAAAGCTTTCTTGT
TGGTAATCAGCTGAGCCTTGCAGATGTGATTTTACTCCAAACCATTTTAGCTCTAGA
AGAGAAAATTCCTAATATCCTGTCTGCATTTCCTTTCCTCCAGGAATACACAGTGAA
ACTAAGTAATATCCCTACAATTAAGAGATTCCTTGAACCTGGCAGCAAGAAGAAGC
CTCCCCCTGATGAAATTTATGTGAGAACCGTCTACAACATCTTTAGGCCATAA

GSTA4 amino acid sequence (SEQ ID NO: 4):

MAARPKLHYPNGRGRMESVRWVLAAAGVEFDEEFLETKEQLYKLQDGNHLLFQQVP
MVEIDGMKLVQTRSILHYIADKHNLFGKNLKERTLIDMYVEGTLDLLELLIMHPFLKPDD
QQKEVVNMAQKAIIRYFPVFEKILRGHGQSFLVGNQLSLADVILLQTILALEEKIPNILSAF
PFLQEYTVKLSNIPTIKRFLEPGSKKKPPPDEIYVRTVYNIFRP

FIG. 18 ralA binding protein 1 mRNA sequence (SEQ ID NO: 5)

```
ATCATTGTAAACAGGCAGAGGCTGGGCGGGGTGGGAATGGGCGCCCGAGGCCGGCCTGGGGCGCAGCGC
AGGAGGCGGCTCCGGTGGCTGCGGCGGCAGCGTGAGCGCGAGGAGGCGGAGGCTGCGGCGGGGCGGACGG
TCGCGCGGCGGCAGGCACAGGTGTAATGGATAGGTAACAGAGAAGACCTCGTCCCTTCCTAGTCAGGGCA
TCAGCATGACTGAGTGCTTCCTGCCCCCACCAGCAGCCCAGTGAACACCGCAGGGTGCAGCATGGCAG
CGGGCTTACCCGGACCCCAGCTCTGAAGAGATCAGCCCTACTAAGTTTCCTGGATTGTACCGCACTGGC
GAGCCCTCACCTCCCCATGACATCCTCCATGAGCCTCCTGATGTAGTGTCTGATGATGAGAAAGATCATG
GGAAGAAAAAGGGAAATTTAAGAAAAAGGAAAAGAGGACTGAAGGCTATGCAGCCTTTCAGGAAGATAG
CTCTGGAGATGAGGCAGAAAGTCCTTCTAAAATGAAGAGGTCCAAGGGAATCCATGTTTTCAAGAAGCCC
AGCTTTTCTAAAAAGAAGGAAAAGGATTTTAAAATAAAAGAGAAACCCAAAGAAGAAAAGCATAAAGAAG
AAAAGCACAAAGAAGAAAAACATAAAGAGAAGAAGTCAAAAGACTTGACAGCAGCTGATGTTGTTAAACA
GTGGAAGGAAAAGAAGAAAAAGAAAAAGCCAATTCAGGAGCCAGAGGTGCCTCAGATTGATGTTCCAAAT
CTCAAACCCATTTTTGGAATTCCTTTGGCTGATGCAGTAGAGAGGACCATGATGTATGATGGCATTCGGC
TGCCAGCCGTTTTCCGTGAATGTATAGATTACGTAGAGAAGTATGGCATGAAGTGTGAAGGCATCTACAG
AGTATCAGGAATTAAATCAAAGGTGGATGAGCTAAAAGCAGCCTATGACCGGGAGGAGTCTACAAACTTG
GAAGACTATGAGCCTAACACTGTAGCCAGTTTGCTGAAGCAGTATTTGCGAGACCTTCCAGAGAATTTGC
TTACCAAAGAGCTTATGCCCAGATTTGAAGAGGCTTGTGGGAGGACCACGGAGACTGAGAAAGTGCAGGA
ATTCCAGCGTTTACTCAAAGAACTGCCAGAATGTAACTATCTTCTGATTTCTTGGCTCATTGTGCACATG
GACCATGTCATTGCAAAGGAACTGGAAACAAAAATGAATATACAGAACATTTCTATAGTGCTCAGCCCAA
CTGTGCAGATCAGCAATCGAGTCCTGTATCTGTTTTTCACACATGTGCAAGAACTCTTTGGAAATGTGGT
ACTAAAGCAAGTGATGAAACCTCTGCGATGGTCTAACATGGCCACGATGCCCACGCTGCCAGAGACCCAG
GCGGGCATCAAGGAGGAGATCAGGAGACAGGAGTTTCTTTTGAATTGTTTACATCGAGATCTGCAGGGTG
GGATAAAGGATTTGTCTAAAGAAGAAAGATTATGGGAAGTACAAAGAATTTTGACAGCCCTCAAAAGAAA
ACTGAGAGAAGCTAAAAGACAGGAGTGTGAAACCAAGATTGCACAAGAGATAGCCAGTCTTTCAAAAGAG
GATGTTTCCAAAGAAGAGATGAATGAAAATGAAGAAGTTATAAATATTCTCCTTGCTCAGGAGAATGAGA
TCCTGACTGAACAGGAGGAGCTCCTGGCCATGGAGCAGTTTCTGCGCCGGCAGATTGCCTCAGAAAAAGA
AGAGATTGAACGCCTCAGAGCTGAGATTGCTGAAATTCAGAGTCGCCAGCAGCACGGCCGAAGTGAGACT
GAGGAGTACTCCTCCGAGAGCGAGAGCGAGAGTGAGGATGAGGAGGAGCTGCAGATCATTCTGGAAGACT
TACAGAGACAGAACGAAGAGCTGGAAATAAAGAACAATCATTTGAATCAAGCAATTCATGAGGAGCGCGA
GGCCATCATCGAGCTGCGCGTGCAGCTGCGGCTGCTCCAGATGCAGCGAGCCAAGGCCGAGCAGCAGGCG
CAGGAGGACGAGGAGCCTGAGTGGCGCGGGGGTGCCGTCCAGCCGCCCAGAGACGGCGTCCTTGAGCCAA
AAGCAGCTAAAGAGCAGCCAAAGGCAGGCAAGGAGCCGGCAAAGCCATCGCCCAGCAGGGATAGGAAGGA
GACGTCCATCTGAGCAGCCTGCGTGGCCGTCTGGAGTCCGTGAGACTGAAAGGACCCGTGCATCTTACTG
TAACCCGGGGGCCAGGCCGGCTCTCTCGCTGTACATTCTGTAAAGGTGTCTTCTCTTCTCAGACTCTTCC
TCTGTCACACGTCTGACTCCTTCACGTCAGGCTCAGGTTCCATGGGAGGACGAAGCAGTGGACGCATTGT
GGGCTTAGGCACAGATCAGTTTTCCAGATAGTGTCAGCTTATTTGAAGATTAATTTCTTTGTTAACTT
AAAATAACTATTTTAACCCTTGAGTGGCTTCTTTTTAAACCAAAACCGTCTTTCTTTGCTTTTTATCA
CAGCAGAATCAGGATCTCTTTCTCATTCAAGGGGGAACCACCCCAGGTCAGCGCTGCGCCTGCTGTGGC
CGCCGCGAGCCACGCCCTCTGGGATCTCTGGTACCGTCACTCTTGCTTGTGCCTTCCACACCTTCTCGGT
```

FIG. 18 continued

```
GCAGATCCCTATGGGGGAGCTGCCTCACGTTCTCTGACTGGTCAGAGCAGCGCCTGGTGGGTGTTCCCTG
GCCCACTCTCCTCTCTCCTTCTGCAGTTCTAAACCACAGTCTATAAGCCCGAGTCACCAGGACGGCCTGT
CTGGCCACAGACAGGGGCTGCCTGTGGAGCCTGCCCACCGGCCCCCGGCAGTGCAGTCCAGCGGGGAGGA
GGCTGCCCGTTCCTGCCAGTTCCTCACTGCGGGGACCAGCAAAGGCCTTCTCACTGGGTTGGTCAAAGGT
AGTCACCTTGGCCTGGTGCATCCACAGAGGATGTTGTTCAAACCAGAAATCTTTTAAACGACTGACCTTC
CTTAAAAACAGAATGACTCCGATTGCTTGCTTGGGCTAGAATGTACACGTCTCCTTGCCTGAATAAGCCA
TATATATGCTCTTAAACAAAAGTTTGAAATTATCCATATCATCTCAGTGAACCTACTGGTGGACTCCCAA
TTGACAAGATTGAGCAATAGAAAAAAATTCCTTTCCTTTGAATGATAGCTGTGATTCACCCCACCCCATT
TTCTTGTTTCTGGTCCATCCGATGAGACGGATGCTCTGATGCTCTGAGGCTTCTGGGAGGCTGGGCCCTG
GAGGCAACGTGCTGCAGGCGCACTCTGTCAGAGTGAACAGCACCGCGAGACAGGCCAGGCTCGTGGCTCG
GAAGACAAACCCCACACACACTCAAGGGGTCGAAAACAAACCCCACACGAGGGCTCTCACCTCCTTCTCC
TAGGTAGTATTTATTTTCAGCACCTGTTTGATGCAGTTTTTAATCCTCTACCTATTGCACTGTTGTGACT
CGTTGGCCATTATTTGATTTTGTACGAAAAAAAGCTTTGTTATAGAAATCAGCATACTATTTTTTTAAA
TCTGGAGACAAGATATTCTGGTGACTGAAAGTATGGTCGGGTGTCAGATATAAATGTGCAAATGCCTTCT
TGCTGTCCTGTCGGTCTCAGTACGTTCACTTTATAGCTGCTGGCAATATCGAAGGTTCCTTTTTTGTTTG
TGTAAACTCTAATTTCTATCAAGGTGTCATGGATTTTTAAAATTAGTATTTCATTACAAATGTCTCAGCA
TTGGTTAACTAATTTTTGCCAGGACCATTATTGATCAAGCAAATAAATTCAACAGCCATTTGGGAAAAAG
AAAAGCTTCTAGTTTTTTTGTACACATTCTTTCTGTGAGGAGATTGAGTACTCTGCAGCTGGCGAGGAGT
TGGTTGAGGCACTTCTTCAAGGCCAAGGGGGAACACAGTGTTTTGTTTCCAGCTCACTTTGTACCCCTCA
CCTCTGCAGACACGGGGAGAACCCCGGACCCCTGGCATGCATGCTGGCGGCGGCATGCCTCCCTTCCACA
AGCCCATGCTGCTGCAGAGGGAGCCTGTGTTTGCAAAACCCAGTGGACTGGGCTGGGTCTGCTGTCTGAG
CAGCTCCTGGCTCCGGTGGGAACTGCACACAAGTCCACTGGCCTGGCTTGGCCCCAGGCATTGCAATTGA
CAGACATTTGCATTTCATACGGTAAATGAGGACTCAGCACAGCCAACCATAATCAGCATGTCTGGGATAG
ACTGGTCTAGAATAAAAATGAAGTTTCCATTGCTTTGTTTGCTTTAAAAATTCCACAATTAAAATATCTG
TCATTGAAAGCTTAAAAAAAAAAAAAAAA
```

FIG. 19

| Primer Name | RT-PCR Primers | SEQ ID: NOs |
|---|---|---|
| insulin-1 Forward | TAGTGACCAGCTATAATCAGAG | SEQ ID NO: 12 |
| insulin-1 Reverse | ACGCCAAGGTCTGAAGGTCC | SEQ ID NO: 13 |
| insulin-2 Forward | CCCTGCTGGCCCTGCTCTT | SEQ ID NO: 14 |
| Insulin-2 Reverse | AGGTCTGAAGGTCACCTGCT | SEQ ID NO: 15 |
| glucagon Forward | GAATTCATTGCTTGGCTGGTGAAAGGC | SEQ ID NO: 16 |
| glucagon Reverse | CATTTCAAACATCCCACGTGGCATGCA | SEQ ID NO: 17 |
| NgN3 Forward | CTGCGCATAGCGGACCACAGCTTC | SEQ ID NO: 18 |
| NgN3 Reverse | CACAAGAAGTCTGAGAACACCAG | SEQ ID NO: 19 |
| PDX1 Forward | CCACCCCAGTTTACAAGCTC | SEQ ID NO: 20 |
| PDX1 Reverse | TGTAGGCAGTACGGGTCCTC | SEQ ID NO: 21 |
| β-actin Forward | CACCCGCGAGTACAACCTTC | SEQ ID NO: 10 |
| β-actin Reverse | CCCATACCCACCATCACACC | SEQ ID NO: 11 |

FIG. 20

| Primer Name | RT-PCR Primers | SEQ ID NOs |
|---|---|---|
| TNFα Forward | TGTTGCCTCCTCTTTTGCTT | SEQ ID NO: 22 |
| TNFα Reverse | TGGTCACCAAATCAGCGTTA | SEQ ID NO: 23 |
| IL-6 Forward | ACAAAGCCAGAGTCCTTCAGAG | SEQ ID NO: 24 |
| IL-6 Reverse | ACCACAGTGAGGAATGTCCAC | SEQ ID NO: 25 |
| MCP-1 Forward | AGGTCCCTGTCATGCTTCTGG | SEQ ID NO: 26 |
| MCP-1 Reverse | CAGCACTTCTTTGGGACACCTGCTG | SEQ ID NO: 27 |
| β-actin Forward | CACCCGCGAGTACAACCTTC | SEQ ID NO: 10 |
| β-actin Reverse | CCCATACCCACCATCACACC | SEQ ID NO: 11 |

FIG. 21

| Primer Name | RT-PCR Primers | SEQ ID: NOs |
|---|---|---|
| RLIP76 Forward | TTCAAGAAGCCCAGCTTTTC | SEQ ID NO: 8 |
| RLIP76 Reverse (497 bp size band) | TCAAAAGAAACTCCTGTCTCCTG | SEQ ID NO: 28 |
| RLIP76 Reverse (894 bp size band) | ATTCTCTGGAAGGTCTCGCA | SEQ ID NO: 9 |

METHODS, COMPOSITIONS, AND KITS FOR IMPROVING PANCREATIC BETA CELL VIABILITY AND TREATING DISEASES OR CONDITIONS RELATED TO BETA CELL DESTRUCTION

PRIORITY CLAIM

This application claims priority to U.S. Provisional Application No. 61/953,725 filed Mar. 14, 2014, which is hereby incorporated by reference as if fully set forth herein.

BACKGROUND

Human islet transplant frequently fails due to apoptosis and necrosis occurring in the cells prior to transplantation. Successful transplantation is hampered by poor survival of transplanted insulin secreting beta (β) cells contained in the islets. Oxidative stress and other stresses are a major cause of decrease in cell or tissue viability and loss or insulin-secretion function prior to transplantation. The success-rate of human islet-cell transplantation is highly dependent on the number of viable insulin-secreting cells transplanted.

Islet transplantation has been successful in treating many patients with type 1 diabetes mellitus. However, this therapeutic procedure is limited because of the chronic shortage of cadaveric pancreata. Therefore, developing methods to increase islet mass by stimulating the proliferation of islet cells in-vitro would have a significant impact for expansion of insulin producing β-cells for transplant applications. Pancreatic β-cells are relatively susceptible to the damaging effects of oxidative stress because of low levels of free-radical quenching enzymes. Thus, there is a need to increase the number of viable insulin-secreting cells as a means for improving tissue or cell transplantation or treating type 1 diabetes mellitus.

SUMMARY

Provided herein in certain embodiments are methods of increasing β-cell viability in a target islet. The methods may include contacting the target islet with a delivery vehicle including a molecule such as a GSTA4 polypeptide having at least 95% sequence identity with an amino acid sequence of SEQ ID NO: 4 or a GSTA4 polynucleotide which encodes the GSTA4 polypeptide. In certain embodiments, contacting the target islet with the delivery vehicle may occur in the media or buffer solution used for isolation, preparation, or storage of the target islet. In certain embodiments, the delivery vehicle may be a liposome, nanoparticle, nanotube, non-liposomal lipid, or polymer and may include the GSTA4 polypeptide. In certain embodiments, the delivery vehicle may further include a RLIP76 polypeptide having at least 95% sequence identity with an amino acid sequence of SEQ ID NO: 2. In certain embodiments, the delivery vehicle may be a plasmid or a viral vector and may include the GSTA4 polynucleotide, the GSTA4 polynucleotide having at least 95% sequence identity with a DNA sequence of SEQ ID NO: 3. In certain embodiments, the delivery vehicle may further include a RLIP76 polynucleotide having at least 95% sequence identity with a DNA sequence of SEQ ID NO: 1. In certain embodiments, the delivery vehicle may be the viral vector comprising an adenovirus vector, an adeno-associated virus vector, a herpes simplex virus vector, a retrovirus vector, or a lentivirus vector.

Also provided herein in certain embodiments are methods of treating a disease or condition in a subject. In certain embodiments, the methods may include steps such as contacting a target islet with a delivery vehicle comprising a molecule comprising a GSTA4 polypeptide having at least 95% sequence identity with an amino acid sequence of SEQ ID NO: 4 or a GSTA4 polynucleotide which encodes the GSTA4 polypeptide and transplanting the target islet into the subject to treat the disease or condition. In certain embodiments, the disease or condition may be type 1 diabetes. In certain embodiments, contacting the target islet with the delivery vehicle may occur in the media or buffer solution used for isolation, preparation, or storage of the target islet. In certain embodiments, the delivery vehicle may be a liposome, nanoparticle, nanotube, non-liposomal lipid, or polymer and may include the GSTA4 polypeptide. In certain embodiments, the delivery vehicle may further include a RLIP76 polypeptide having at least 95% sequence identity with an amino acid sequence of SEQ ID NO: 2. In certain embodiments, the delivery vehicle may be a plasmid or a viral vector and may include the GSTA4 polynucleotide, the GSTA4 polynucleotide having at least 95% sequence identity with a DNA sequence of SEQ ID NO: 3. In certain embodiments, the delivery vehicle may further include a RLIP76 polynucleotide having at least 95% sequence identity with a DNA sequence of SEQ ID NO: 1. In certain embodiments, the delivery vehicle may be the viral vector comprising an adenovirus vector, an adeno-associated virus vector, a herpes simplex virus vector, a retrovirus vector, or a lentivirus vector.

Also provided herein in certain embodiments are kits to increase β-cell viability in a target islet. In certain embodiments, the kits may include a delivery vehicle and a molecule including a GSTA4 polypeptide having at least 95% sequence identity with an amino acid sequence of SEQ ID NO: 4 or a GSTA4 polynucleotide which encodes the GSTA4 polypeptide. In certain embodiments, the kit may include the GSTA4 polypeptide and may further include a RLIP76 polypeptide having at least 95% sequence identity with an amino acid sequence of SEQ ID NO: 2. In certain embodiments, the kit may include the GSTA4 polynucleotide and may further include a RLIP76 polynucleotide having at least 95% sequence identity with a DNA sequence of SEQ ID NO: 1. In certain embodiments, the target islet may be transplanted into a subject. In certain embodiments, the delivery vehicle may include a viral vector, plasmid, liposome, nanoparticle, nanotube, non-liposomal lipid, or polymer.

Provided herein in certain embodiments are methods of increasing β-cell viability in a target islet. The methods may include contacting the target islet with a delivery vehicle including a molecule such as a RLIP76 polypeptide having at least 95% sequence identity with an amino acid sequence of SEQ ID NO: 2 or a RLIP76 polynucleotide which encodes the RLIP76 polypeptide. In certain embodiments, contacting the target islet with the delivery vehicle may occur in the media or buffer solution used for isolation, preparation, or storage of the target islet. In certain embodiments, the delivery vehicle may be a liposome, nanoparticle, nanotube, non-liposomal lipid, or polymer and may include the RLIP76 polypeptide. In certain embodiments, the delivery vehicle may further include a GSTA4 polypeptide having at least 95% sequence identity with an amino acid sequence of SEQ ID NO: 4. In certain embodiments, the delivery vehicle may be a plasmid or a viral vector and may include the RLIP76 polynucleotide, the RLIP76 polynucleotide having at least 95% sequence identity with a DNA sequence of SEQ ID NO: 1. In certain embodiments, the delivery vehicle may further include a GSTA4 polynucleotide having at least 95% sequence identity with a DNA sequence of SEQ ID NO: 3. In certain embodiments, the delivery vehicle may be the viral vector comprising an adenovirus vector, an adeno-associated virus vector, a herpes simplex virus vector, a retrovirus vector, or a lentivirus vector.

Also provided herein in certain embodiments are methods of treating a disease or condition in a subject. In certain embodiments, the methods may include steps such as contacting a target islet with a delivery vehicle comprising a molecule comprising a RLIP76 polypeptide having at least 95% sequence identity with an amino acid sequence of SEQ ID NO: 2 or a RLIP76 polynucleotide which encodes the RLIP76 polypeptide and transplanting the target islet into the subject to treat the disease or condition. In certain embodiments, the disease or condition may be type 1 diabetes. In certain embodiments, contacting the target islet with the delivery vehicle may occur in the media or buffer solution used for isolation, preparation, or storage of the target islet. In certain embodiments, the delivery vehicle may be a liposome, nanoparticle, nanotube, non-liposomal lipid, or polymer and comprises the RLIP76 polypeptide. In certain embodiments, the delivery vehicle may further include a GSTA4 polypeptide having at least 95% sequence identity with an amino acid sequence of SEQ ID NO: 4. In certain embodiments, the delivery vehicle may be a plasmid or a viral vector and may include the RLIP76 polynucleotide, the RLIP76 polynucleotide having at least 95% sequence identity with a DNA sequence of SEQ ID NO: 1. In certain embodiments, the delivery vehicle may further include a GSTA4 polynucleotide having at least 95% sequence identity with a DNA sequence of SEQ ID NO: 3. In certain embodiments, the delivery vehicle may be the viral vector comprising an adenovirus vector, an adeno-associated virus vector, a herpes simplex virus vector, a retrovirus vector, or a lentivirus vector.

Also provided herein in certain embodiments are kits to increase β-cell viability in a target islet. In certain embodiments, the kits may include a delivery vehicle and a molecule including a RLIP76 polypeptide having at least 95% sequence identity with an amino acid sequence of SEQ ID NO: 2 or a RLIP76 polynucleotide which encodes the RLIP76 polypeptide. In certain embodiments, the kit may include the RLIP76 polypeptide and may further include a GSTA4 polypeptide having at least 95% sequence identity with an amino acid sequence of SEQ ID NO: 4. In certain embodiments, the kit may include the RLIP76 polynucleotide and may further include a GSTA4 polynucleotide having at least 95% sequence identity with a DNA sequence of SEQ ID NO: 3. In certain embodiments, the target islet may be transplanted into a subject. In certain embodiments, the delivery vehicle may include a viral vector, plasmid, liposome, nanoparticle, nanotube, non-liposomal lipid, or polymer.

BRIEF DESCRIPTION OF THE DRAWINGS

FIG. 6A: Expression of GSTA4 or Ral-binding protein-1 (RALBP1 gene product, also known as Ral-interacting protein (RLIP76)) in control, empty vector (pcDNA3.1) and GSTA4 (GSTA4/pcDNA3.1) transfected INS-1 cells. Several G418-resistant stable clones expressing GSTA4 or RLIP76 were characterized by RT-PCR.

FIG. 6B: A bar graph showing the fold change of the RT-PCR products described in FIG. 6A.

FIG. 6C: Gene specific primers were used for reverse transcription using RT kit (Applied Biosystems).

FIG. 6D: Immunocytochemistry showing INS-1 cells transfected with either control, empty vector (pcDNA3.1) or GSTA4 (GSTA4/pcDNA3.1).

FIG. 13A shows cells transfected with control.

FIG. 13B shows cells transfected with control.

FIG. 13C shows cells transfected with GSTA4.

FIG. 13D shows cells transfected with GSTA4.

FIG. 13E shows cells transfected with RLIP76.

FIG. 13F shows cells transfected with RLIP76.

FIG. 13I(B). Western blot analysis of the RLIP76-transfected dissociated cells.

FIG. 16: DNA sequence of RLIP76 (SEQ ID NO: 1) and amino acid sequence of RLIP76 (SEQ ID NO: 2).

FIG. 17: DNA sequence of GSTA4 (SEQ ID NO: 3) and amino acid sequence of GSTA4 (SEQ ID NO: 4).

FIG. 18: Messenger RNA (mRNA) sequence of *Homo sapiens* ralA binding protein 1 (SEQ ID NO: 5).

FIG. 19: Table of the gene specific primers used for RT-PCR to determine expression of genes involved in insulin signaling in control and GSTA4 transfected cells (see FIG. 8 for data from RT-PCR).

FIG. 20: Table of mouse gene-specific primers used for RT-PCR to determine expression of inflammatory genes (see FIG. 5 for data from RT-PCR).

FIG. 21: Table of RLIP76 gene-specific primers used for RT-PCR to determine RLIP76 expression in dissociated cells (see FIG. 13IA for RT-PCR data). The forward primer for RLIP76 was used in combination with the RLIP76 Reverse (497 bp size band) or the RLIP76 Reverse (894 bp size band) primer.

DETAILED DESCRIPTION

Figure 1A:
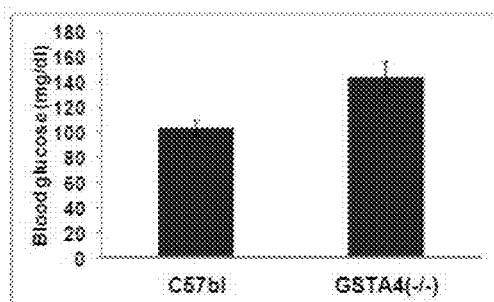
FIG. 1A: Blood glucose levels in C57BL-6 and glutathione S-transferase A4 isoenzyme (GSTA4) knockout mice. Results of blood glucose (fasting) by tail vein blood from one separate determination is shown.
Figure 1B:
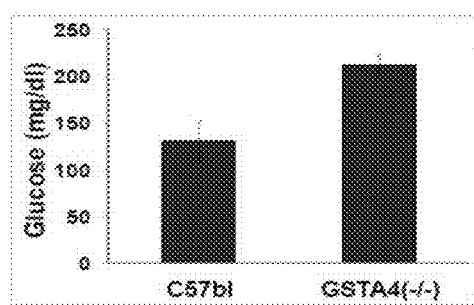
FIG. 1B: Blood glucose levels in C57BL-6 and glutathione S-transferase A4 isoenzyme (GSTA4) knockout mice. Results of blood glucose (fasting) by tail vein blood from one separate determination is shown.
Figure 1C:
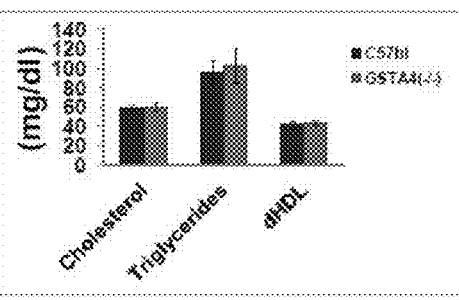
FIG. 1C. Serum lipids for the wild-type (C57Bl-6, black bar) and GSTA4 knockout (GSTA4(−/−), grey) mice.

The following description is merely intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

According to certain embodiments, methods, compositions, and kits are provided herein to increase islet cell viability and to treat a disease or condition caused by the destruction of β-cells in islets, such as type 1 diabetes mellitus. In certain embodiments, islet cells may be β-cells, which are cells in the pancreas located in the islets of Langerhans that function to store and release insulin. In certain embodiments, the methods described herein may include increasing the quantity of enzymes of the mercapturic acid pathway (MaP), such as Ral-binding protein-1 (RALBP1 gene product, also known as Ral-interacting protein (RLIP)), glutathione S-transferase A4 isoenzyme (GSTA4), or a combination thereof, in islets. RLIP refers to all splice-variants of the protein-product encoded by human RALBP1 including, but not limited to, the predominant 76 kDa splice variant known as RLIP76.

As shown in the Example below, increasing the quantity of RLIP76 or GSTA4 in islets may result in an increase in the ability of such islets to survive in-vitro prior to transplantation and to survive in humans in whom islets are transplanted. In certain embodiments, the quantity of RLIP76 polypeptides and/or GSTA4 polypeptides in islets may be increased through delivery of RLIP76 polypeptides and/or GSTA4 polypeptides as described herein or RLIP76 polynucleotides and/or GSTA4 polynucleotides as described herein to the islets.

MaP enzymes function as defenses against oxidative stress. The examples provided herein demonstrate that augmenting the activity of the MaP by increasing the MaP enzymes including RLIP76 or human GSTA4 leads to an increase in the viability and insulin-secreting ability of pancreatic islet cells. The MaP has been shown to be the primary defense against oxidative stress and electrophilic lipid alkenals, such as 4-OH-t-2-nonenal (4HNE), generated during oxidative stress and metabolized primarily to glutathione-electrophile conjugates. GSTA4 and RLIP76 are the two major determinants of 4HNE levels in cells. Furthermore, RLIP76 is the rate limiting enzyme for both MaPs and clathrin dependent endocytosis which regulates the signaling of insulin and other peptide-hormones. Over-expression of GSTA4 has shown to increase the proliferation of normal epithelial cells to >50%. Therefore, targeting GSTA4 and RLIP76 to increase survival and proliferation of β-cells may have clinical utility in preserving and maintaining functional β-cell mass in early onset type 1 diabetics and in protecting newly formed or regenerated β-cells from destruction and providing functional β-cells for islet transplantation. The results provided herein demonstrate improved survival and reduced apoptosis in islet cells augmented with RLIP76 or GSTA4. Characterization of β-cells for cell mass and insulin sensitivity in GSTA4 and RLIP76 knockout mice clearly showed the central role of these enzymes in insulin-sensitivity and β-cell survival.

The MaP utilizes glutathione (GSH) for biotransformation of chemicals into mercapturic acids that are excreted in the urine. The MaP has long been known to play a key role in metabolism and excretion of mutagenic electrophilic chemicals (deficient in a pair of electrons) derived from exogenous sources (poisons, xenobiotics) and metabolites of xenobiotics (benzo[a]pyrene) or drugs (acetaminophen) (Jakoby 1978; Awasthi 1994). The importance of this pathway in the metabolism and excretion of endogenously derived electrophiles generated from the oxidative metabolism of polyunsaturated fatty acids (PUFA) has been increasingly recognized more recently (Sharma 2004). Through studies over the past two decades, the role of various glutathione S-transferases (that catalyze the first committed step of this pathway) in defending cells from pro-apoptotic and mutagenic effects of PUFA-derived reactive oxidant and electrophilic compounds has been elucidated. These studies have shown the importance of the alpha class GST isoenzymes (GSTA) as excellent catalysts for reductive metabolism of lipid-hydroperoxides originating from PUFA (Yang 2002). Through these studies, the key role of a specific alpha-class enzyme, GSTA4, in metabolism of the toxic and mutagenic reactive aldehydes that are byproducts of peroxidation of PUFA has been identified. 4HNE is the predominant reactive aldehyde produced from peroxidation of PUFA, and is the preferred substrate for GSTA4. GSTA4 catalyzes the formation of the glutathione (GSH)-4HNE adduct which must be subsequently transported out of cells by RLIP76 before it can be further metabolized to a mercapturic acid. The GSTA4 knockout mouse was created and showed that lack of this enzyme causes an increase in 4HNE in mouse tissues (Engle 2004). Subsequently, the major MaP pathway transporter, RLIP76 was identified and cloned. The knockout mouse lacking RLIP76 has a much greater level of oxidative stress (Awasthi 2005; Warnke 2008).

Since loss of RLIP76 in knockout mice is known to increase blood and tissue markers of oxidative stress, and oxidative stress has been implicated as a direct cause of type 2 diabetes, insulin-resistance and hyperlipidemia, the glycemic control and blood lipid levels in these mice was studied. Surprisingly, instead of insulin-resistance, as would be predicted from high levels of oxidative stress, marked insulin-sensitivity was found in these knockout mice. On the basis of this, a novel mechanism for insulin-resistance was proposed based on stress-induced induction of RLIP76 and consequent enhanced inactivation of insulin-signaling through the clathrin-dependent endocytosis (CDE) pathway (Awasthi 2010; Singhal 2011; Singhal 2011b; Singhal 2013). Because insulin-resistance is also implicated as a pathogenic mechanism in obesity, the hypothesis that the insulin-sensitivity of the RLIP76 knockout mice should cause a resistance to obesity was subsequently tested. These studies confirmed resistance to diet induced obesity of these mice (Singhal 2013). As part of these studies, the effect of RLIP76 knockout on blood insulin levels and on pancreatic islet cells which make and secrete insulin was investigated. Consistent with the known sensitivity to oxidative stress of islet cells, smaller pancreatic islets and lower insulin content of the islets were found.

However, the studies from the RLIP76 knockout mice did not fully answer the question of whether aberrant glycemic control in these mice was simply due to the deficient function of the MaP, or due more specifically to the loss of CDE in which RLIP76 plays a crucial catalytic role. Thus, the experiments in Example 1 below were performed to characterize the glycemic control mechanisms in the GSTA4 knockout mice, which are partially deficient in the MaP, but have a normal CDE mechanism.

The studies provided herein show a glycemic control mechanism in GSTA4 and the effect of MaP enzymes on the viability of islet cells. This is the first demonstration of a role of GSTA4 in regulating islet cell viability, insulin-secretion, as well as the regulation of expression of genes that control insulin-secretion. The studies described herein also provide a novel model of type 1 diabetes.

As provided in Example 1 below, similar to the results shown previously in the RLIP76 knockout mouse, the GSTA4 knockout mouse also had smaller islets and reduced plasma insulin levels. Although oxidative stress is known to be increased in both RLIP76 and GSTA4 knockout mice, their phenotype with respect to glycemic control were quite distinct. Whereas the RLIP76 knockout mouse is a model of insulin sensitivity (hypoglycemia despite low insulin levels), the GSTA4 knockout mice is diabetic, with normal insulin-sensitivity, a very interesting model for type 1 diabetes. Also, unlike the RLIP76 knockout mouse which is hypolipidemic, serum lipids in the GSTA4 knockout mouse were unaltered. The GSTA4 knockout mouse is also characterized by histological evidence of tissue damage, elevated liver enzymes, and increased cytokines.

As shown in Example 1 below, augmenting either RLIP76 or GSTA4 in cultured INS-1 cells reduced apoptosis and protected cells from oxidative stress, which is the first demonstration of these effects of MaP enzyme augmentation in islet cells. Thus, as provided herein, increasing the expression or quantity of these enzymes in human islets transplanted to treat type 1 diabetes enzymes should improve the efficacy of islet cell transplantation. Results provided herein showed markedly improved ability of human islets to survive in-vitro cell culture upon augmentation of MaP enzymes, which indicates the potential human application of this approach for improving islet cell transplantation.

The ability of MaP enzymes to induce proliferation of INS-1 cells and to increase insulin production is very novel and of high significance. The observations provided herein regarding the ability of GSTA4 to cause up-regulation of insulin-regulatory transcription factor is highly novel and may be applicable in the future for other possible novel applications. Because islet cells stably overexpressing GSTA4 may be immortalized and continuously self-replicating, and insulin-secretion by the islet cells could be controlled by regulating GSTA4 expression, they may be useful to treat type 1 diabetes if they were encapsulated in nano-tubes and transplanted into human with type 1 diabetes. The secretion of insulin by these cells could be controlled using drugs such as tetracycline by using a tetracycline-responsive promoter upstream of the GSTA4 gene.

According to certain embodiments herein, methods, compositions, and kits herein are provided to increase islet cell viability. In certain embodiments, the islet cell may be a β-cell. In certain embodiments, increasing islet cell viability includes, without limitation, increasing insulin secretion by β-cells in islets, increasing survival of islet cells, preserving and maintaining functional β-cell mass of islets, increasing proliferation of islet cells, reducing apoptosis, and/or reducing oxidative stress in islet cells. As discussed herein and supported by the Example below, increasing the quantity of RLIP76 or GSTA4 protein in islets to be transplanted or in transplanted islets may result in an increase in the ability of such islets to survive in-vitro prior to transplantation and to survive in humans in whom islets are transplanted.

According to certain embodiments, increasing islet cell viability may be accomplished by increasing the expression or quantity of RLIP76 polypeptides, GSTA4 polypeptides, or a combination thereof in the islets. Accordingly, in certain embodiments, the expression or quantity of RLIP76 polypeptides, GSTA4 polypeptides, or a combination thereof (i.e., RLIP76 polypeptides and GSTA4 polypeptides) in islets may be increased through delivery of RLIP76 polypeptides, GSTA4 polypeptides, or a combination thereof (i.e., RLIP76 polypeptides and GSTA4 polypeptides) or RLIP76 polynucleotides, GSTA4 polynucleotides, or a combination thereof (i.e., RLIP76 polynucleotides and GSTA4 polynucleotides) to the islets. It is also contemplated that both polynucleotides (i.e., GSTA4 and RLIP76) and polypeptides (i.e., GSTA4 and RLIP76) described herein may be delivered to islets in order to increase viability of islets.

In certain embodiments, an "islet" or "target islet" may include, without limitation, a human cadaver islet, an islet of a subject, an islet to be transplanted into a subject, or an islet transplanted into a subject. An "islet" or a "target islet" includes populations of cells which produce hormones in response to glucose levels, including β-cells.

RLIP76 is a multifunctional protein that is encoded in humans on chromosome 18p11.3 by a gene with 11 exons and 9 introns (see NCBI Reference Sequence: NM_006788 and SEQ ID NO: 5 (FIG. 18) for the mRNA sequence of the Homo sapiens ralA binding protein 1). The protein product of the gene is typically a 76 kDa protein (i.e., RLIP76); however, splice-variants including a 67 kDa polypeptide and longer 80 kDa or 102 kDa polypeptides have also been identified. In certain embodiments, it is contemplated that other splice-variants may be used in place of RLIP76 in the embodiments described herein.

According to certain embodiments herein, a RLIP76 polypeptide may comprise, consist of, or consist essentially of the amino acid sequence as provided in SEQ ID NO: 2 (i.e., human RLIP76 amino acid sequence, NCBI Reference Sequence: NP_006779.1, see FIG. 16). In certain embodiments, a RLIP76 polypeptide may be GMP-grade, for example, the GMP-grade RLIP76 produced in large scale by Terapio Inc., Austin, Tex. In certain embodiments, a RLIP76 polynucleotide may be any polynucleotide that encodes an RLIP76 polypeptide as described herein. In certain embodiments, a RLIP76 polynucleotide may comprise, consist or, or consist essentially of a DNA sequence provided in SEQ ID NO: 1 (i.e., RLIP76 DNA sequence, see FIG. 16). In certain embodiments, a RLIP76 polynucleotide may be a RLIP76 gene.

According to certain embodiments herein, a GSTA4 polypeptide may comprise, consist of, or consist essentially of the amino acid sequence as provided in SEQ ID NO: 4 (i.e., human GSTA4 amino acid sequence, NCBI Reference Sequence: NP_001503.1, see FIG. 17). In certain embodiments, a GSTA4 polynucleotide may be any polynucleotide that encodes a GSTA4 polypeptide as described herein. In certain embodiments, a GSTA4 polynucleotide may comprise, consist or, or consist essentially of the DNA sequence provided in SEQ ID NO: 3 (i.e., GSTA4 DNA sequence, see FIG. 17). In certain embodiments, a GSTA4 polynucleotide may be a GSTA4 gene.

In certain embodiments, the polynucleotides described herein may be recombinant or non-naturally occurring polynucleotides. In certain embodiments, the polynucleotides described herein may be messenger RNA (mRNA) or DNA. In certain embodiments, the polynucleotides may be cDNA.

Polynucleotides as described herein are not limited to the functional region of the nucleotide sequence, and may include at least one of an expression suppression region, a coding region, a leader sequence, an exon, an intron, and an expression cassette (see, e.g. Papadakis et al., "Promoters and Control Elements: Designing Expression Cassettes for Gene Therapy," Current Gene Therapy (2004), 4, 89-113). Further, polynucleotides may include double stranded DNA, single stranded DNA or RNA. The RLIP76 polynucleotides and GSTA4 polynucleotides described herein may be fragments or mutants of the full length RLIP76 polynucleotides or GSTA4 polynucleotides, respectively. A fragment means a part of the polynucleotide that encodes a polypeptide which provides substantially the same function as the polypeptide encoded by the full-length polynucleotide. Examples of polynucleotide mutants include naturally occurring allelic mutants; artificial mutants; and polynucleotide sequences obtained by deletion, substitution, addition, and/or insertion of one or more nucleotides to the polynucleotide sequence. It should be understood that such a fragment and/or mutant of a polynucleotide sequence encodes a polypeptide having substantially the same function as a polypeptide encoded by the original full-length polynucleotide sequence. For example, a fragment and/or mutant of a RLIP76 polynucleotide encodes a RLIP76 polypeptide that possesses substantially the same function of a full length RLIP76 polypeptide and a fragment and/or mutant of a GSTA4 polynucleotide encodes a GSTA4 polypeptide that possesses substantially the same function of a full length GSTA4 polypeptide.

In certain embodiments, it is contemplated that RLIP76 polypeptides and GSTA4 polypeptides as described herein may include modifications in their amino acid sequences or chemical modifications in their structures formulated for use with or without a delivery vehicle, such as those described herein (e.g., liposomes, nanoparticles, etc.).

According to certain embodiments herein, a polypeptide or amino acid sequence described herein may have at least 90%, at least 91%, at least 92%, at least 93%, at least 94%, at least 95%, at least 96%, at least 97%, at least 98%, at least 99%, about 90%, about 91%, about 92%, about 93%, about 94%, about 95%, about 96%, about 97%, about 98%, about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% sequence identity with SEQ ID NO: 2 or SEQ ID NO: 4. For example, in certain embodiments, a GSTA4 polypeptide used with the methods, compositions, or kits as described herein may have at least 95% sequence identity with an amino acid sequence of SEQ ID NO: 4. In certain embodiments, a RLIP76 polypeptide used with the methods, compositions, or kits as described herein may have at least 95% sequence identity with an amino acid sequence of SEQ ID NO: 2.

According to certain embodiments herein, a polynucleotide or DNA sequence described herein may have at least 90%, at least 91%, at least 92%, at least 93%, at least 94%, at least 95%, at least 96%, at least 97%, at least 98%, at least 99%, about 90%, about 91%, about 92%, about 93%, about 94%, about 95%, about 96%, about 97%, about 98%, about 99%, about 90%~99.999%, about 91%~99.999%, about 92%~99.999%, about 93%~99.999%, about 94%~99.999%, about 95%~99.999%, about 96%~99.999%, about 97%~99.999%, about 98%~99.999%, or about 99%~99.999% sequence identity with SEQ ID NO: 1 or SEQ ID NO: 3. For example, in certain embodiments, a GSTA4 polynucleotide used with the methods, compositions, or kits as described herein may have at least 95% sequence identity with a DNA sequence of SEQ ID NO: 3. In certain embodiments, a RLIP76 polynucleotide used with the methods, compositions, or kits as described herein may have at least 95% sequence identity with a DNA sequence of SEQ ID NO: 1.

Codon optimization is a technique that may be used to maximize the protein expression in an organism by increasing the translational efficiency of the gene of interest. Different organisms often show particular preferences for one of the several codons that encode the same amino acid due to mutational biases and natural selection. For example, in fast growing microorganisms such as *E. coli*, optimal codons reflect the composition of their respective genomic tRNA pool. Therefore, the codons of low frequency of an amino acid may be replaced with codons for the same amino acid but of high frequency in the fast growing microorganism. Accordingly, the expression of the optimized DNA sequence is improved in the fast growing microorganism. See, e.g. http://www.guptalab.org/shubhg/pdf/shubhra_codon.pdf for an overview of codon optimization technology, which is incorporated herein by reference in its entirety. As provided herein, the DNA sequences described herein may be codon optimized for optimal polypeptide expression in a particular type of cell line including, but not limited to, mammalian cells.

In certain embodiments, a delivery vehicle may be used to deliver a RLIP76 polynucleotide and/or GSTA4 polynucleotide to a target islet. In certain embodiments, the delivery vehicle may include, without limitation, viral vectors, plasmids, liposomes, nanoparticles, nanotubes, non-liposomal lipids, and/or polymers. In certain embodiments, the delivery vehicle may include any delivery vehicle known to one skilled in the art for delivering polypeptides or polynucleotides to a cell.

In certain embodiments, an increase in RLIP76 and/or GSTA4 expression in a target islet may occur through genetic or epigenetic methods, which includes, without limitation, partial or stable transfection or transduction of the respective full length gene or DNA sequence into the target islet.

In certain embodiments, a RLIP76 polynucleotide and/or GSTA4 polynucleotide may be delivered to a target islet via transfection, in which the RLIP76 polynucleotide and/or GSTA4 polynucleotide is introduced into the target islet either transiently or permanently (also called persistent or stable). In certain embodiments, transfection of the target islet may occur using non-viral transfection delivery vehicles including, but not limited to, a plasmid, liposome, nanoparticle, nanotube, non-liposomal lipid, or polymer. For example, in certain embodiments, a tetracycline-controlled transcriptional activation plasmid may be used to deliver the RLIP76 polynucleotides and/or GSTA4 polynucleotides to the target islets and further control expression of the transfected polynucleotides. In certain embodiments, the tetracycline-controlled transcriptional activation plasmid may include a tetracycline-responsive promoter upstream of the RLIP76 polynucleotides and/or GSTA4 polynucleotides in the plasmid.

In certain embodiments, a RLIP76 polynucleotide and/or GSTA4 polynucleotide may be delivered to a target islet via virus-mediated transfection (i.e., transduction), in which the RLIP76 polynucleotide and/or GSTA4 polynucleotide is introduced into the target islet. Transduction may be either transient or permanent (also called persistent or stable). In certain embodiments, viral vectors may be used to transduce a target islet. In certain embodiments, the viral vectors may include an adenovirus vector, an adeno-associated virus vector, a herpes simplex virus vector, a retrovirus vector, or a lentivirus vector.

In certain embodiments, a RLIP76 polypeptide and/or GSTA4 polypeptide may be delivered to a target islet via a delivery vehicle including, without limitation, a liposome, nanoparticle, nanotube, non-liposomal lipid, or polymer. For example, in certain embodiments, a RLIP76 polypeptide and/or GSTA4 polypeptide may be encapsulated in liposomes and delivered to a target islet to increase the quantity of the RLIP76 polypeptide and/or GSTA4 polypeptide in the target islet.

The novel findings described herein offer strong evidence for the feasibility of using RLIP76 protein and/or GSTA4 protein as an additive to islet preparation medium for preservation of the viability of human islets for transplantation. In certain embodiments, delivery of a RLIP76 and/or GSTA4 polypeptide or a RLIP76 and/or GSTA4 polynucleotide to a target islet may be performed in a media or buffer used for isolation, preparation or storage of the target islets. In certain embodiments, it is also contemplated that certain chemical agents known to increase polynucleotide or polypeptide expression of RLIP76 and/or GSTA4 may be added to the media or buffer used for isolation, preparation or storage of islets in order to increase expression of RLIP76 and/or GSTA4.

According to certain embodiments, methods of treating a disease or condition in a subject are also provided herein. In certain embodiments, a "disease or condition" as described herein may be, without limitation, a disease or condition caused by a decrease in islet cell viability (e.g., β-cell viability), a destruction of β-cells, and/or a decrease in β-cell insulin secretion. In certain embodiments, a disease or condition may be diabetes mellitus or a peptide hormone deficiency. In certain embodiments, diabetes mellitus may be type 1 diabetes mellitus. In certain embodiments, a disease or condition may include any disease or condition that relates to a β-cell deficiency.

In certain embodiments, methods of treating a disease or condition in a subject may comprise delivering a RLIP76 polynucleotide and/or GSTA4 polynucleotide to a target islet, and transplanting the target islet into the subject to treat the disease or condition. In certain embodiments, methods of treating a disease or condition in a subject may comprise delivering a RLIP76 polypeptide and/or GSTA4 polypeptide to a target islet, and transplanting the target islet into the subject to treat the disease or condition. In certain embodiments, the RLIP76 polynucleotide and/or GSTA4 polynucleotide or RLIP76 polypeptide and/or GSTA4 polypeptide may be delivered to a target islet using any of the methods and delivery vehicles as described herein. For example, in certain embodiments, the delivery vehicle used for delivering the polypeptides or polynucleotides as described herein may include, without limitation, any delivery vehicle known to one skilled in the art for delivering polypeptides or polynucleotides to a cell including, without limitation, viral vectors, plasmids, liposomes, nanoparticles, nanotubes, non-liposomal lipids, or polymers. In certain embodiments, the delivery of the RLIP76 polynucleotide and/or GSTA4 polynucleotide may be transient or permanent. In certain embodiments, a RLIP76 polynucleotide and/or GSTA4 polynucleotide or a RLIP76 polypeptide and/or GSTA4 polypeptide may be added to islet isolation, storage or preparation media prior to transplantation of the islet into the subject.

In certain embodiments, methods of treating a disease or condition in a subject may comprise administering a therapeutically effective amount of a RLIP76 polynucleotide and/or GSTA4 polynucleotide or a RLIP76 polypeptide and/or GSTA4 polypeptide to an islet of the subject to treat the disease or condition. The therapeutically effective amount of a RLIP76 polynucleotide and/or GSTA4 polynucleotide or a RLIP76 polypeptide and/or GSTA4 polypeptide may be administered using any of the delivery vehicles described herein. The treatment may be used to treat any disease or condition as described herein. The RLIP76 polypeptides and/or GSTA4 polypeptides or RLIP76 polynucleotides and/or GSTA4 polynucleotides described herein may be administered alone or as part of a composition comprising the polypeptides or polynucleotides. The compositions may also include any one or more delivery vehicles that are described herein. The compositions may be delivered in any effective manner and may be delivered and/or utilized alone or in combination with another therapy.

In certain embodiments, the methods described herein may be used with other MaP enzymes.

"Treating" or "treatment" of a disease or condition may refer to preventing the disease or condition, slowing the onset or rate of development of the disease or condition, reducing the risk of developing the condition, preventing or delaying the development of symptoms associated with the disease or condition, reducing or ending symptoms associated with the disease or condition, generating a complete or partial regression of the disease or condition, or some combination thereof. Treatment may also mean a prophylactic or preventative treatment of a disease or condition.

A "subject in need thereof" as used herein with regard to a disease or condition refers to a human subject who has previously been diagnosed with a disease or condition, is suspected of having a disease or condition, and/or a subject who has previously exhibited one or more symptoms associated with a disease or condition.

The phrases "patient" and "subject" are used interchangeably herein.

The term "effective amount" as used herein refers to an amount of a RLIP76 polypeptide and/or a GSTA4 polypeptide or a RLIP76 polynucleotide and/or a GSTA4 polynucleotide described herein that produces a desired effect. For example, a population of cells may be contacted with an effective amount of a RLIP76 polypeptide and/or a GSTA4 polypeptide or a RLIP76 polynucleotide and/or a GSTA4 polynucleotide described herein to study its effect in vitro (e.g., cell culture) or to produce a desired therapeutic effect ex vivo or in vitro. An effective amount of a RLIP76 polypeptide and/or a GSTA4 polypeptide or a RLIP76 polynucleotide and/or a GSTA4 polynucleotide described herein may be used to produce a therapeutic effect in a subject, such as preventing or treating a target disease or condition, alleviating symptoms associated with the disease or condition, or producing a desired physiological effect. In such a case, the effective amount of a RLIP76 polypeptide and/or a GSTA4 polypeptide or a RLIP76 polynucleotide and/or a GSTA4 polynucleotide described herein is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of a RLIP76 polypeptide and/or a GSTA4 polypeptide or a RLIP76 polynucleotide and/or a GSTA4 polynucleotide described herein (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether a RLIP76 polypeptide and/or GSTA4 polypeptide or RLIP76 polynucleotide and/or GSTA4 polynucleotide described herein is administered alone or in combination with another polypeptide or polynucleotide, compound, drug, therapy or other therapeutic method or modality. One skilled in the clinical and pharmacological arts will be able to determine an effective amount or therapeutically effective amount through routine experimentation, namely by monitoring a cell's or subject's response to administration of a RLIP76 polypeptide and/or GSTA4 polypeptide or a RLIP76 polynucleotide and/or a GSTA4 polynucleotide described herein and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005, which is hereby incorporated by reference as if fully set forth herein.

A "pharmaceutically acceptable carrier" as used herein refers to a pharmaceutically acceptable material, composition, or delivery vehicle that is involved in delivering a RLIP76 polypeptide and/or a GSTA4 polypeptide or a RLIP76 polynucleotide and/or a GSTA4 polynucleotide as described herein of interest to a cell, tissue or organ (i.e., pancreas). A pharmaceutically acceptable carrier may comprise a variety of components, including but not limited to a liquid or solid filler, diluent, excipient, solvent, buffer, encapsulating material, surfactant, stabilizing agent, binder, or pigment, or some combination thereof. Each component of the carrier must be "pharmaceutically acceptable" in that it must be compatible with the other ingredients of the composition and must be suitable for contact with any cell, tissue or organ that it may encounter, meaning that it must not carry a risk of toxicity, irritation, allergic response, immunogenicity, or any other complication that excessively outweighs its therapeutic benefits.

Examples of pharmaceutically acceptable carriers for use in the compositions provided herein include, but are not limited to, (1) sugars, such as lactose, glucose, sucrose, or mannitol; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols such as propylene glycol; (11) polyols such as glycerin, sorbitol, mannitol and polyethylene glycol; (12) esters, such as ethyl oleate and ethyl laurate; (13) disintegrating agents such as agar or calcium carbonate; (14) buffering or pH adjusting agents such as magnesium hydroxide, aluminum hydroxide, sodium chloride, sodium lactate, calcium chloride, and phosphate buffer solutions; (15) alginic acid; (16) pyrogen-free water; (17) isotonic saline; (18) Ringer's solution; (19) alcohols such as ethyl alcohol and propane alcohol; (20) paraffin; (21) lubricants, such as talc, calcium stearate, magnesium stearate, solid polyethylene glycol, or sodium lauryl sulfate; (22) coloring agents or pigments; (23) glidants such as colloidal silicon dioxide, talc, and starch or tri-basic calcium phosphate; (24) other non-toxic compatible substances employed in pharmaceutical compositions such as acetone; and (25) combinations thereof.

The term "about" as used herein means within 5% or 10% of a stated value or range of values.

Provided herein in certain embodiments are kits for carrying out the assays and methods disclosed herein. The kits disclosed herein may include a RLIP76 polypeptide and/or a GSTA4 polypeptide or a RLIP76 polynucleotide and/or a GSTA4 polynucleotide as described herein. The kits may additionally include any delivery vehicle that can be used to deliver a RLIP76 polypeptide and/or a GSTA4 polypeptide or a RLIP76 polynucleotide and/or a GSTA4 polynucleotide to an islet. The kits may additionally include other pigments, binders, surfactants, buffers, stabilizers, and/or chemicals. In certain embodiments, the kits may additionally include substances that may be used for testing levels of RLIP76 polynucleotides and/or GSTA4 polynucleotides or RLIP76 polypeptides and/or GSTA4 polypeptides. In certain embodiments, the kits may include substances that may be used for testing insulin and glucose levels in serum. In certain embodiments, the kits provided herein comprise instructions in a tangible medium.

One of ordinary skill in the art will recognize that the various embodiments described herein can be combined. For example, steps from the various methods of treatment disclosed herein may be combined in order to achieve a satisfactory or improved level of treatment.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Targeting the Mercapturic Acid Pathway to Improve β-Cell Survival and Proliferation Effect of GSTA4 Gene Knockout in C57BL-6 Mice.

The studies of glycemic regulation in RLIP76 gene knockout mice revealed very unexpected findings of insulin-sensitivity, hypoglycemia, low-cholesterol and resistance to obesity, which are essentially the opposite of metabolic syndrome that would have been expected because of a high level of tissue oxidative stress in these mice (Awasthi 2005; Warnke 2008; Awasthi 2010; Singhal 2011a; Singhal 2011 b; Singhal 2013). Thus, it could not be predicted whether a GSTA4 knockout, which also exhibits oxidative stress (but no CDE abnormalities), would have altered blood glucose or insulin levels, or any effects on their pancreatic islets. To address these questions, the first known studies of glycemic control in GSTA4 knockout mice were performed, as created by Yang 2002. Unlike the results in RLIP76 knockout mice, the 8 week old GSTA4 knockout mice were actually hyperglycemic; in addition, unlike RLIP76 knockout animals that had decreased serum cholesterol and triglycerides, these lipids as well as HDL-cholesterol were unaffected in these animals. However, similar to what was previously seen in the RLIP76 knockout mice, serum insulin was decreased in the GSTA4 knockout mice (see FIG. 1). This decrease of approximately 50% in serum insulin level seen in GSTA4 knockout mice was less dramatic (~75%) than what was seen in the RLIP76 knockout mice.

Taken together, the elevated glucose and low insulin level in the GSTA4 knockout mouse indicated that these mice have a phenotype consistent with type 1 diabetes. The ratio of glucose/insulin is nearly the same in wild-type and GSTA4 knockout mice, indicating that the hyperglycemia is not due to insulin-resistance. This is of particular interest because no previous genetic alterations (knockout or transgenic) have yielded a similar mouse. The previous models are driven primarily by genetic alterations that lead to immune mediated pancreatic islet destruction that occur gradually over the life-span of the mouse (20-40 weeks) or drug-induced destruction of pancreatic islets using streptozotocin, a chemotherapy drug that causes islet cell death due to oxidative stress-mediated apoptosis. The blood glucose and lipid alterations in the GSTA4 knockout mice are novel. In addition, because GSTA4 is not involved in CDE and CDE is not affected in these mice, the mechanism of diabetes is likely related to deficient pancreatic insulin production or secretion rather than to peripheral insulin-resistance.

Figure 2:
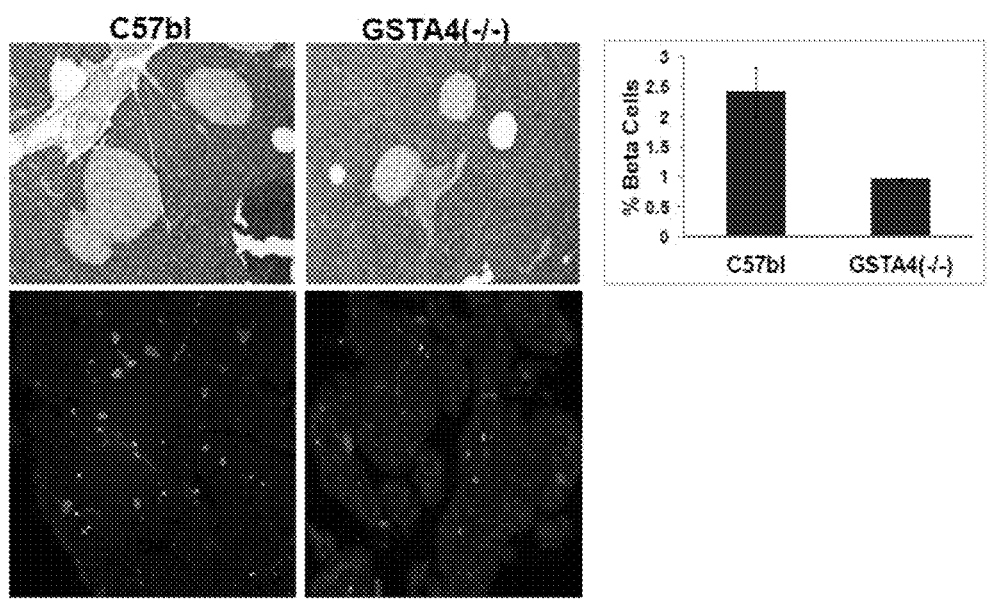
FIG. 2: Insulin levels and the pancreatic β-cell mass in C57BL-6 and GSTA knockout mice. Pancreas were stained for hematoxylin and eosin (H&E). The % of β-cell values for n=3 is presented in the bar graph.
Figure 3:
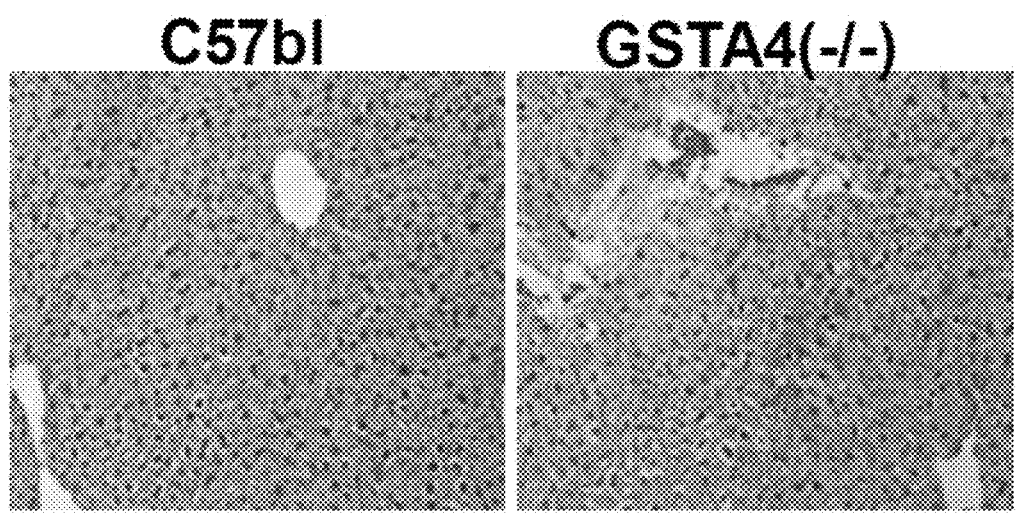
FIG. 3: Pancreatic histology of GSTA4 knockout mice. Formalin fixed pancreas from C57BL-6 and GSTA4 knockout mice were sectioned and stained for H&E.
Figure 4A:
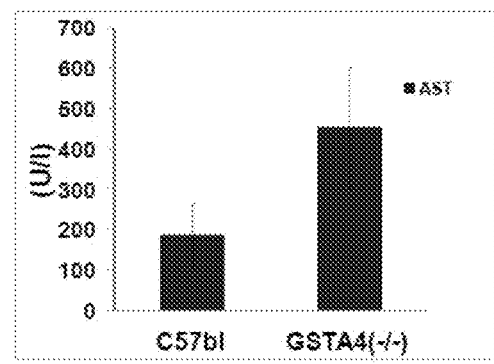
FIG. 4A: Serum liver enzymes for C57BL-6 and GSTA4 knockout mice. Serum levels of AST are presented.
Figure 4B:
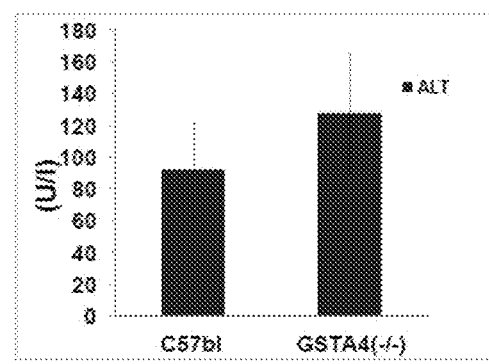
FIG. 4B. Serum liver enzymes for C57BL-6 and GSTA4 knockout mice. Serum levels of ALT are presented.

The reason for decreased insulin levels was examined by studying the size and insulin-content of the pancreatic islets. Histological examination of hematoxylin-eosin slides of the pancreas showed that their islets were significantly smaller in the GSTA4 knockout mouse. Examination of insulin stained pancreatic tissue by fluorescence microscopy at low power confirmed the decreased number and size of the islets. Quantitation of insulin staining confirmed a significantly reduced islet cell mass (FIG. 2). Higher magnification analysis of hematoxylin-eosin stained sections of pancreatic tissues revealed significantly disorganized pancreatic tissue, without significant inflammatory cell infiltration (FIG. 3). Measurements of serum levels of AST and ALT enzymes were also found to be increased in the GSTA4 knockout mice (FIG. 4). Though most frequently used as markers of liver damage, these enzymes are also a generalized measure of damage to tissues, including the pancreas. Histological examination of other organs did not reveal significant damage, suggesting that the pancreas is particularly susceptible to the loss of GSTA4.

Because oxidative-stress or inflammation promoting cytokines secreted by the liver have generalized pro-inflammatory effects that have been shown to adversely affect pancreatic tissue, the expression of three of these genes, IL-6, TNFα, and MCP1 was measured in liver tissues. Results of these studies showed marked elevation of IL-6 and TNFα (see FIG. 5). In contrast MCP-1, and inflammatory and immune regulatory cytokine secreted by monocytes, macrophages and dendritic cells was not altered. These findings suggest that oxidative-stress itself rather than inflammation play a greater role in damage to the pancreas in the GSTA4 knockout mice. These findings indicated that GSTA4 plays a significant role in protection of the pancreas as well as pancreatic islets by reducing oxidative stress.

The Effect of Over-Expression MaP Genes in Rat INS-1 Cell Line.

Figure 1D:
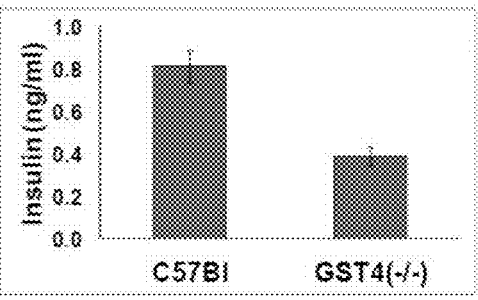
FIG. 1D. Serum insulin level for the wild-type (C57Bl-6) and GSTA4 knockout (GSTA4(−/−)) mice.

To examine the mechanisms through which the MaP enzymes protect islet cells, the effect of GSTA4 or RLIP76 over-expression was examined in INS-1, a rat insulinoma derived cell line which is an widely accepted model for studies of islet cells because of the inability to culture non-transformed islet-cells in cell culture models. GSTA4 or RLIP76 were over-expressed in INS-1 cells by transfection with pcDNA3.1 eukaryotic expression vector. Northern blot analysis of total RNA extracted confirmed successful transfection. The Northern blots and their densitometric quantitation from these studies showed successful over-expression of GSTA4 in three selected clones and of RLIP76 in one clone (FIGS. 6A and B, respectively) (see FIG. 6C for primer sequences used for reverse transcription). Immunohistochemical staining for GSTA4 transfection confirmed increased enzyme expression (FIG. 1D).

Figure 7A:
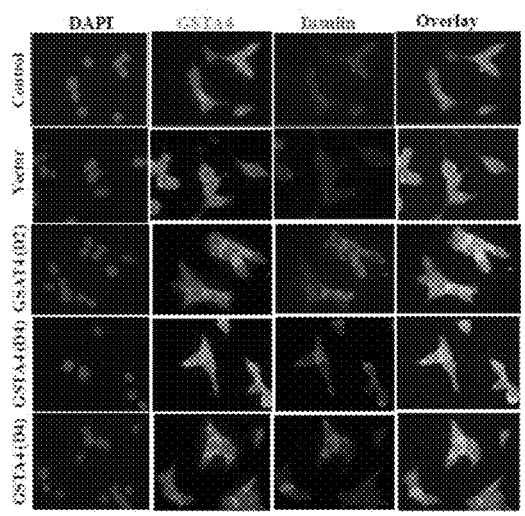
FIG. 7A: Expression of GSTA4 and Insulin in INS-1 cells. A. Immunocytochemistry showing DAPI, GSTA4, and insulin staining in cells transfected with control, vector, or GSTA4.
Figure 7B:
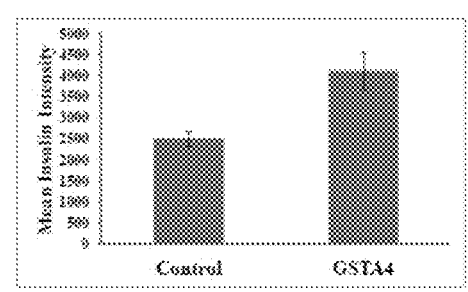
FIG. 7B: Expression of insulin in INS-1 cells. A bar graph showing the mean insulin intensity of cells. The values of n=3 are presented.
Figure 8:
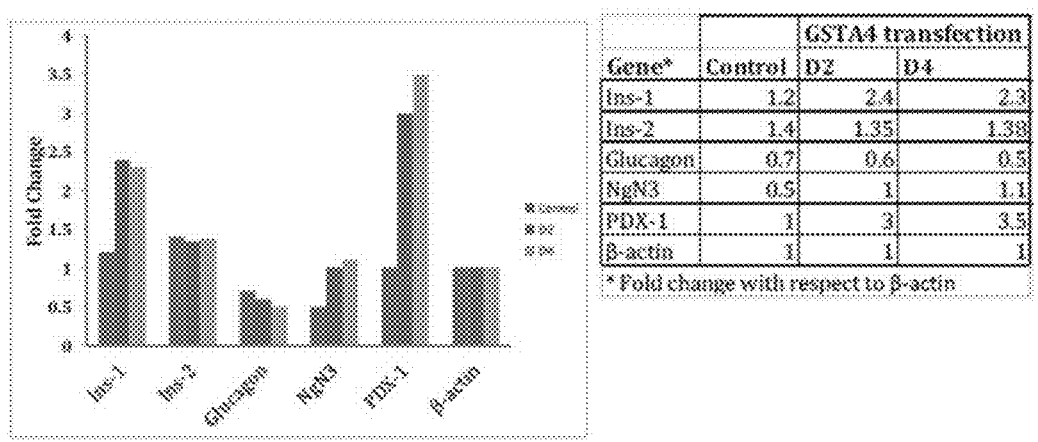
FIG. 8: Expression of genes involved in insulin signaling in control and GSTA4 transfected cells. A bar graph showing the fold change of expression of genes involved in insulin signaling as determined by RT-PCR. The left bar (medium grey) represents data from the control, the middle bar (dark grey) represents gene expression from clone D2 expressing GSTA4, and the right bar (light grey) represents gene expression from clone D4 expressing GSTA4.

The effect of GSTA4 over-expression of the insulin-levels in these cells was examined by immunohistochemistry. These studies showed a significantly increased intracellular content of insulin by fluorescence microscopy (FIG. 7A) and was confirmed by scanning densitometry for insulin staining (FIG. 7B). The potential mechanism for increased insulin production in these cells was examined by using RT-PCR to compare the expression of genes known to encode insulin and to regulate insulin expression. Mice are known to have two insulin genes, both responsive to glucose levels; they differ because Ins-1 expression is insensitive to oxidative-stress whereas the expression of Ins-2 is suppressed by oxidative-stress. Because GSTA4 suppresses oxidative-stress, it was predicted that Ins-1 should be up-regulated in GSTA4 over-expressing cells. This prediction was verified by results of RT-PCR showing over-expression of Ins-1 and no effect on Ins-2 mRNA (FIG. 8, bar graph). These findings suggest that the lower levels of insulin in GSTA4 knockout mice may be due to oxidative stress that results in a differential decrease in the expression of the Ins-1 gene. The mechanism of the altered transcription may be due to increases in the NgN3 and PDX-1 transcription factors that regulate insulin gene expression. In contrast, glucagon expression, which is inversely related to insulin expression, was decreased as expected. These findings are the first demonstration of the ability of MaP enzymes to regulate insulin content of islet cells, the differential increase in Ins-1 expression due to suppression of oxidative-stress by GSTA4 and that increases in GSTA4 may affect insulin expression through effects on PDX-1 and NgN3.

Effect of Gene Over-Expression on Cellular Oxidative Stress.

Figure 9:
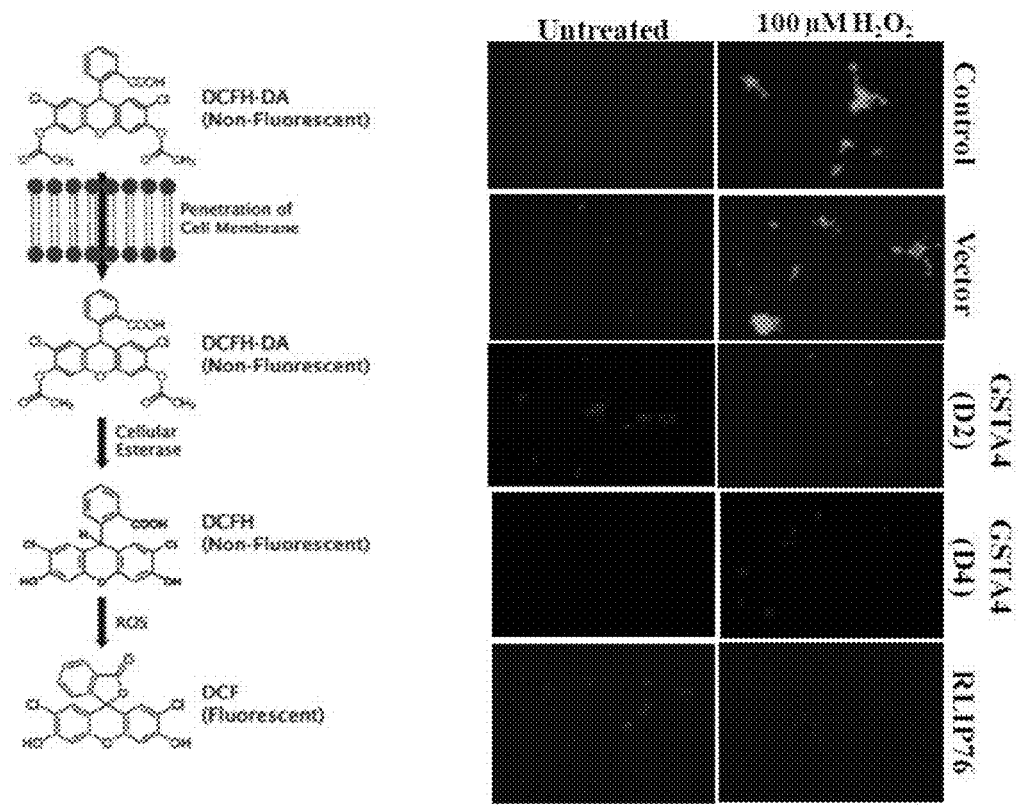
FIG. 9: GSTA4 overexpression protects INS-1 cells from oxidative stress. A schematic shows the process of treating cells with $H_2O_2$ to induce oxidative stress. Fluorescence of cells is shown after treatment with $H_2O_2$ as described.
Figure 10:
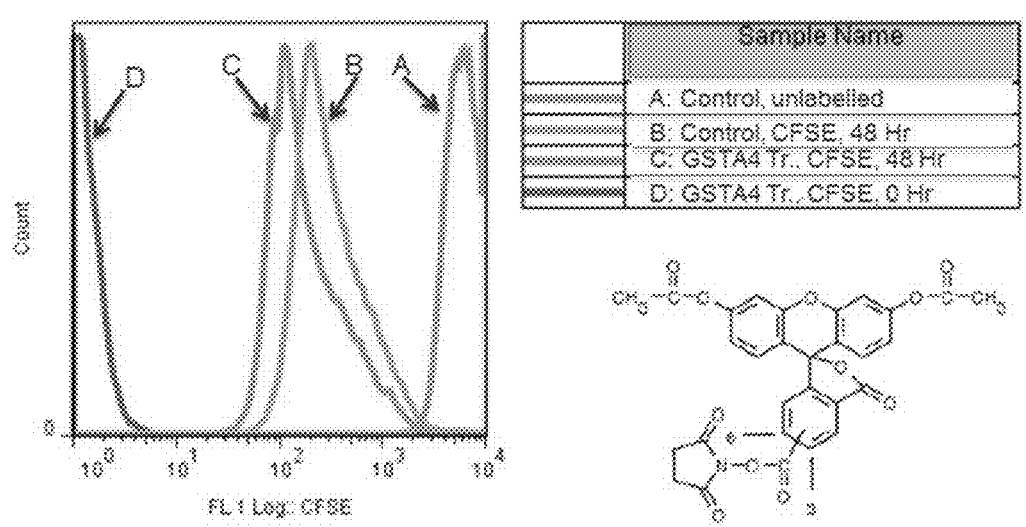
FIG. 10: Effect of GSTA4 transfection on proliferation of INS-1 cells. Flow cytometry data shows the overexpression of GSTA4 prevents the cells from $H_2O_2$ induced oxidative stress (see trace labeled C).

Pancreatic islets are particularly susceptible to oxidative stress, and drugs that cause oxidative stress are known to ablate pancreatic islets in rats and mice, rendering them diabetic. The mercapturic acid pathway is known to reduce cellular oxidative stress. To ensure that the overexpression of these enzymes did indeed have this known effect and that the observed effects on insulin expression were due to this effect, the effect of oxidative stress was measured in a standard fashion, after exposure to hydrogen-peroxide in cells with over-expression of GSTA4 or RLIP76. The fluorescent cytochemistry method that was used employed the dichloro-dihydro-fluorescein diacetate (DCFH-DA) fluorescent dye that reacts with free-radicals. The chemical basis of this widely accepted method is shown (FIG. 9, see schematic). Results of these studies showed that both GSTA4 and RLIP76 proteins conferred significant protection from oxidative stress (FIG. 9). The protection from oxidative stress by GSTA4 transfection was confirmed by flow-cytometric measurement of oxidative-stress using DCFA-DA (FIG. 10). The effect of oxidative stress-mediated apoptosis was also examined by flow-cytometry using dual labeling with propidium iodide and annexin V. Results of these studies showed that hydrogen peroxide exposure caused apoptosis, that it was suppressed by GSTA4 or RLIP76 transfection (see FIG. 11). These results are novel because this is the first study showing that augmenting cellular GSTA4 or RLIP76 suppresses apoptosis in islet cells. These results are significant because they imply that augmenting RLIP76 or GSTA4 in islet cells could prevent apoptosis, particularly in the context of islet-cell transplantation where the isolation and processing of human cadaveric pancreas islet results in significant loss or viable islets due to oxidative stress.

Effect of Gene Over-Expression on Cell Proliferation.

Figure 12:
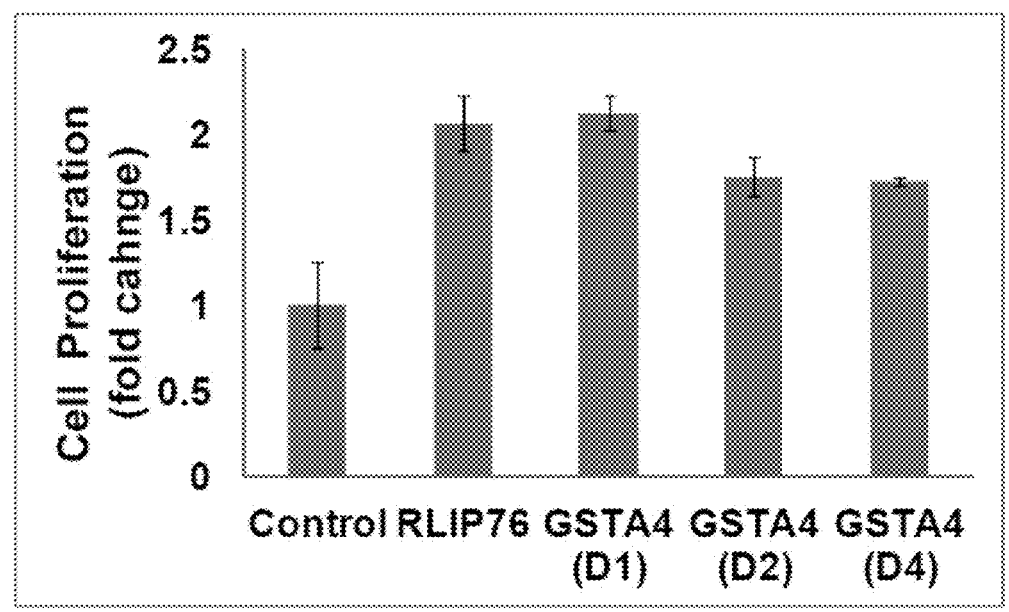
FIG. 12: Effect of GSTA4 or RLIP76 transfection on proliferation of INS-1 cells. A bar graph shows the cell proliferation results of a 3-(4,5-dimethylthiazol-2-yl)-2,5-diphenyl-2H-tetrazolium Bromide (MTT) assay. Fold change was normalized to control cells.

It was previously shown that other types of cells (retinal pigment epithelial, leukemia, lung cancer, etc.) are stimulated to proliferate upon over-expression of GSTA4 or RLIP76. To ensure that a similar effect was present in INS-1 cells, the effects of enzyme over-expression on cell proliferation was determined by MTT assay. These results demonstrated doubling of proliferation in cells overexpressing either of these proteins (FIG. 12). These results are novel because they are the first demonstration of increased cell proliferation of an islet derived cell by over-expression of MaP enzymes.

Effect of RLIP76 on Survival of Human Pancreatic Islets in Culture.

Figure 13:
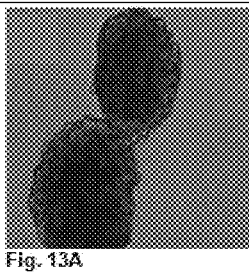
FIG. 13A: Effect of MaP enzyme transfection on human pancreatic islet cultures. The change of morphology at day 20 of the islets is shown at 20× magnification.
FIG. 13B: Effect of MaP enzyme transfection on human pancreatic islet cultures. The change of morphology at day 20 of the islets is shown at 20× magnification.
FIG. 13C: Effect of MaP enzyme transfection on human pancreatic islet cultures. The change of morphology at day 20 of the islets is shown at 20× magnification.
FIG. 13D: Effect of MaP enzyme transfection on human pancreatic islet cultures. The change of morphology at day 20 of the islets is shown at 20× magnification.
FIG. 13E: Effect of MaP enzyme transfection on human pancreatic islet cultures. The change of morphology at day 20 of the islets is shown at 20× magnification.
FIG. 13F: Effect of MaP enzyme transfection on human pancreatic islet cultures. The change of morphology at day 20 of the islets is shown at 20× magnification.
FIG. 13G: Effect of MaP enzyme transfection on human pancreatic islet cultures. The change of morphology at day 20 of the islets is shown at 20× magnification. After 25 days, the RLIP76-transfected islets were dissociated by trypsinization and grown in culture medium containing 11 mM glucose and 100 µg/mL G418. Cell morphology was determined by phase contrast microscopy (note cell division in G).
FIG. 13H: Effect of MaP enzyme transfection on human pancreatic islet cultures. The change of morphology at day 20 of the islets is shown at 20× magnification. After 25 days, the RLIP76-transfected islets were dissociated by trypsinization and grown in culture medium containing 11 mM glucose and 100 µg/mL G418. Cell morphology was determined by phase contrast microscopy.
FIG. 13I(A): A gel showing the RT-PCR results of the expression of RLIP76 in the RLIP76-transfected dissociated cells using two pair of gene specific primers (see FIG. 21 for primers).

The results showing decreased apoptosis as well as increased proliferation are of significance because it demonstrates that it could be used to improve survival of human cadaveric pancreatic islet cells during and after isolation, prior to transplant. It is well known that in culture, human islets (consisting of clusters of hundreds to thousands of cells) do not proliferate. Intact islets isolated from human cadaveric pancreas were obtained from Department of Diabetes, Endocrinology and Metabolism, City of Hope through IIDP distribution center, under the approved IRB (11159). The islets (~200 IEQ) were cultured in six well plates pre-coated with HTB-9 human bladder carcinoma cell matrix prepared as previously described (Jakoby 1994). Each plate was transfected with eukaryotic expression vector (pcDNA3.1) alone or containing RLIP76 or GSTA4 using Lipofectamine 2000 transfection reagent (Invitrogen) following the manufacturer's instructions. After 5 days, the islets were selected by addition of G418 (100 µg/ml) in the medium. The change in morphology of the islets was determined by taking the images every day using phase contrast microscopy (Olympus AX50). The change of morphology at day 20 of the islets is shown at 20× magnification (FIGS. 13 A-F). After 25 days, islets transfected with RLIP76 were dissociated by trypsin-treatment and were grown into pre-coated six well plate in culture medium containing 11 mM glucose and 100 µg/mL G418. Cell morphology was determined by phase contrast microscopy. RLIP76 transfected dissociated islet cells started to proliferate in culture and dividing cells were observed (FIGS. 13 G, H). The continued expression of islets in these cells was confirmed by RT-PCR (FIG. 13 I).

Effect of RLIP76 Over-Expression on Proliferation of Human Islet Cell In-Vitro.

Figure 14:
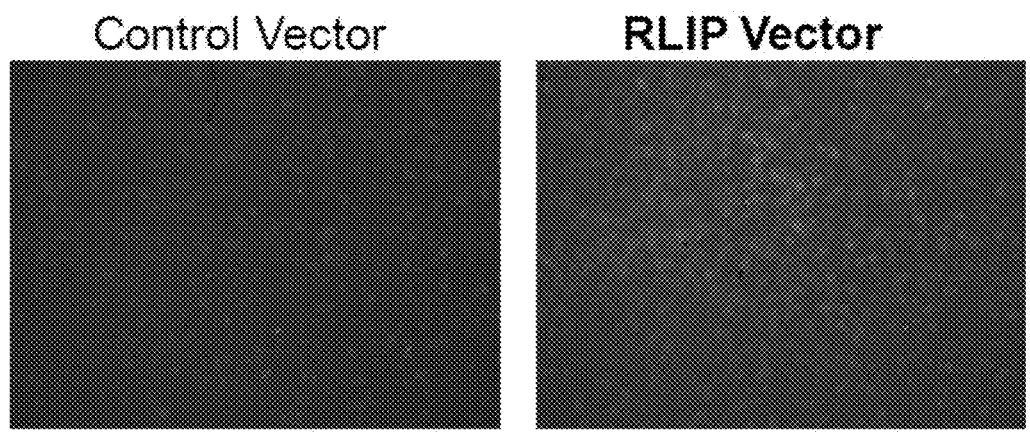
FIG. 14: Effect of RLIP76 over-expression on proliferation of human islet cells in-vitro. Photomicrographs of cultured islet cells taken at 5 days after transient transfection of pcDNA-3 eukaryotic plasmid vector without or with full-length RLIP76.

Human islet cell isolated from human cadaveric pancreas (IRB#11159) were dissociated and placed in cell culture, followed 24 hours later by transient transfection of pcDNA-3 eukaryotic plasmid vector without or with full-length RLIP76 (see FIG. 14).

Effect of RLIP76-Liposomes on Proliferation of Human Islet Cells In-Vitro.

Intact human islets isolated from human cadaveric pancreas (IRB#11159) were dissociated and placed in cell culture. The controls were treated with empty liposomes and experimental with RLIP76-liposomes at 40 μg/mL. Photomicrographs at 20× magnification of human islets isolated from human cadaveric pancreas that treated with RLIP76-liposomes at 40 μg/mL at day 5 and day 10 (see FIG. 15). The photographs demonstrate continued viability and progressive appearance of peripheral adherent cells at 5 and 10 days. The islets in control cultures began to shrink and all islets had disintegrated at 5 days (data not shown).

Materials and Methods

Blood Glucose and Insulin Level in C57Bl-6 and GSTA4 Knockout Mice.

Blood was collected by heart puncture and transferred into Eppendorf tubes on ice, and centrifuged at 3000×g for 10 min. The serum was collected and the serum glucose and lipids were determined (FIG. 1). Insulin levels were determined using the "Ultrasensitive Mouse Insulin ELISA" kit (Crystal Chem Inc.) following the manufacturer's instructions.

Insulin Level and the Pancreatic β-Cell Mass in Control and GSTA Knockout Mice.

Formalin fixed pancreas from wild-type C57BL-6 and GSTA4 knockout mice were sectioned and stained for hematoxylin and eosin (H&E) (FIG. 2). H&E staining was performed for the overall morphology and size of the islets. β-cell mass was determined by quantifying insulin-positive areas in nonadjacent sections at 50 μm intervals throughout the sections according to protocol using laser scanning microscope (iCys LSC, iCys 3.4 software, 40× objective and 0.5 mm step 405, 488, 561 and 630 laser). Contour was based on DAPI stained nuclei and peripheral max and/or max pixel intensity.

Pancreatic Histology of GSTA4 Knockout Mice.

Formalin fixed pancreas from C57BL-6 and GSTA4 knockout mice were sectioned and stained for hematoxylin and eosin (H&E) (FIG. 3). The slides were viewed under Olympus BX51 microscope at pictures at 20× resolution are presented. H&E staining was performed for the overall morphology and size of the islets.

Serum Liver Enzymes in GSTA4 Knockout Mice.

Blood was collected by heart puncture and transferred into Eppendorf tubes on ice, centrifuged at 3000×g for 10 min, and serum was separated from the blood cells. The serum level of AST (FIG. 4A) and ALT (FIG. 4B) was performed.

Expression of Inflammation Marker Genes.

Figure 5:
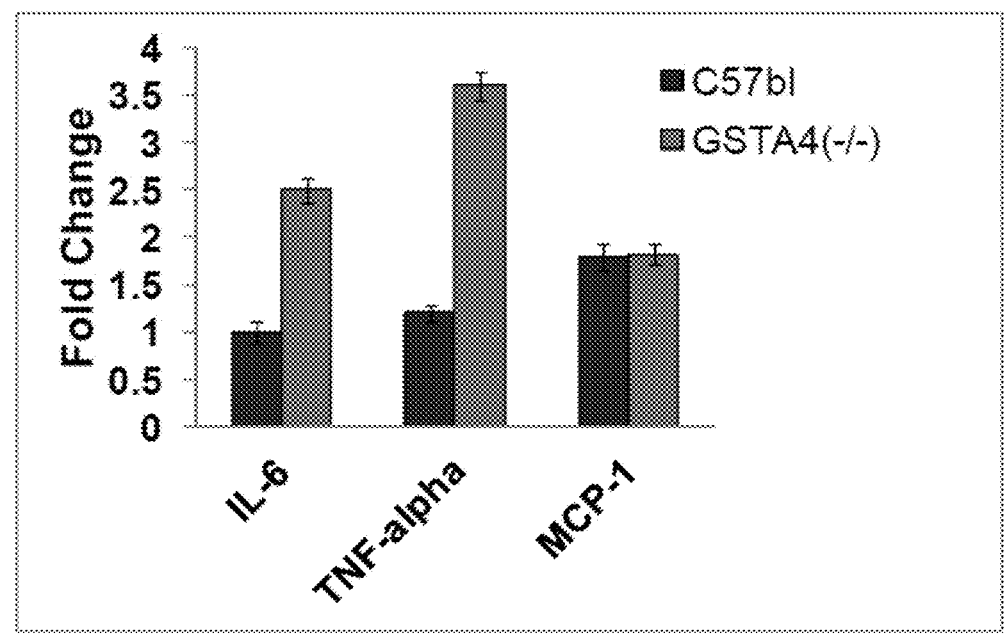
FIG. 5: The expression of inflammation marker genes, IL-6, TNF-alpha, MCP-1, for C57BL-6 (black) and GSTA4 knockout mice (grey).

The expression of inflammatory genes was determined by RT-PCR using mouse gene-specific primers (FIG. 5). Briefly, 1 μg of total RNA from liver tissue was used to synthesize cDNA by reverse transcription using RT kit (Applied Biosystems). The primers for RT-PCR are provided in FIG. 20.

Expression of GSTA4 or RLIP76 in Control, Empty Vector (pcDNA3.1) and GSTA4 (GSTA4/pcDNA3.1) Transfected INS-1 Cells.

INS-1 cells at a density of 1×10$^5$ cells per well were seeded in 12 well tissue culture plate. At >70% confluence, cells were transfected with pcDNA3.1 vector alone (1 μg/well) or pcDNA3.1 vector containing open reading frame (ORF) of the hGSTA4 sequence (GSTA4/pcDNA3.1), or RLIP76 (RLIP76/pcDNA3.1) using Lipofectamine-2000 transfection reagent as per the manufacturer's instructions. Stable transfectant cells were isolated by selection on 200 μg/mL G418 for 2 weeks. Single clones of stably transfected cells were obtained by limited dilution. Further characterization of the several G418-resistant stable clones expressing GSTA4 or RLIP76 was achieved by RT-PCR (FIGS. 6A and B, respectively) and immunocytochemistry (FIG. 6D). RNA prepared using Trizol-reagent (Invitrogen) was quantified and purity determined by measuring absorbance at 260 and 280 nm using a nano-drop spectrophotometer (Thermo Scientific). Gene specific primers (FIG. 6C) were used for reverse transcription using RT kit (Applied Biosystems).

Expression of GSTA4 and Insulin in INS-1 Cells.

Expression of insulin was determined in INS-1 cells (control) and GSTA4 transfected by immunocytochemistry using anti-rat GSTA4 (raised in chicken) and anti-insulin (raised in guinea pig) IgG. DAPI was used as a nuclear stain (FIG. 7A). The slides were also stained and scanned for insulin content (FIG. 7B) using laser scanning microscope (iCys LSC, iCys 3.4 software, 40× objective and 0.5 mm step 405, 488, 561 and 630 laser). Contour based on DAPI stained nuclei and peripheral max and/or max pixel intensity.

Expression of Genes Involved in Insulin Signaling in Control and GSTA4 transfected cells.

Expression of genes involved in insulin signaling was determined by RT-PCR using gene specific primers as shown in the Table in FIG. 19. Expression of genes was determined by RT-PCR and quantified by densitometry using Alpha Imager (see FIG. 8).

GSTA4 Overexpression Protects INS-1 Cells from Oxidative Stress.

INS-1 cells: control, or stably transfected with empty vector (pcDNA3.1), GSTA4 (GSTA4/pcDN3.1) or RLIP76 (RLIP76/pcDNA3.1) were grown on cover-slips and incubated with 1 mM DFCH-DA at 37° C. in a $CO_2$ incubator. After 60 min, the cells were treated with 100 μM $H_2O_2$ and were incubated for 30 min. Cells were washed 2 times with PBS and cover-slips were mounted and observed under a fluorescence microscope (Olympus BX51) using excitation and emission wavelengths of 480 nm and 530 nm, respectively (FIG. 9).

Effect of GSTA4 Transfection on Proliferation of INS-1 Cells.

CellTrace™ CFSE cell proliferation kit was used for staining the cells and analyzed by flow cytometry. Briefly, 1×10$^6$ cells were incubated for 15 min with 20 μM CSFE in complete medium in $CO_2$ incubator at 37° C., washed 2 times with pre-warmed media and grown for 72 hours in standard culture media. Cells were harvested and analyzed by flow cytometry following manufacturer instructions (Life Technologies). Dichloro-dihydro-fluorescein diacetate (DCFH-DA) was used for the quantification of oxidative stress in $H_2O_2$ treated control and transfected cells (FIG. 10).

Effect of GSTA4 and RLIP76 Transfection on Protection of INS-1 Cells from $H_2O_2$ induced cell apoptosis by flow cytometry.

Figure 11:
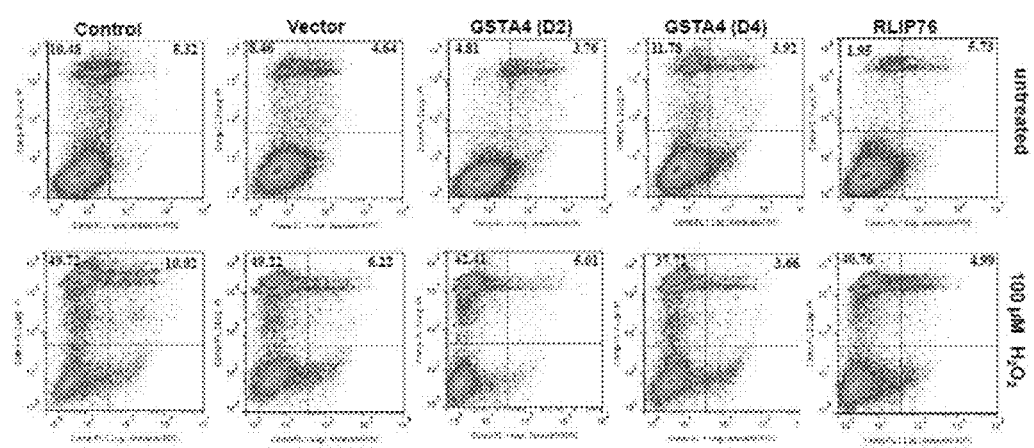
FIG. 11: Effect of GSTA4 and RLIP76 transfection on protection of INS-1 cells from $H_2O_2$ induced cell apoptosis by flow cytometry. Representative results for one of three independent measurements are presented. The statistical comparison showed that the difference in apoptotic fraction was significant for both enzymes (vector vs. GSTA4 transfected, $p<0.01$ and vector vs. RLIP76 transfected cell, $p<0.01$).

INS-1 cells (1×10$^6$ cells/ml) were grown in a 6-well plate and treated with 100 μM $H_2O_2$ for 30 min, harvested and centrifuged at 1500×g for 5 min. Cells were washed with PBS and resuspended in 400 μl of cold annexin binding buffer containing 5 μL of Annexin V-FITC (BD Biosciences) and 5 μL of 0.1 mg/mL propidium iodide. Cells were incubated at room temperature for 10 min in the dark and were analyzed by flow cytometry. Results were processed using FloJo analysis software (FIG. 11).

Effect of GSTA4 or RLIP76 Transfection on Proliferation of INS-1 Cells.

Cell proliferation was determined by 3-(4,5-dimethylthiazol-2-yl)-2,5-diphenyl-2H-tetrazolium Bromide (MTT) assay as described before. Briefly, 50,000 cells were plated in 24 well tissue culture treated plate and grown in standard culture media. After 48 h incubation, 20 μL of a stock solution of MTT (5 mg/mL in PBS) was added to each well and the plates were incubated for additional 4 h at 37° C., centrifuged, and the medium was decanted. Cells were subsequently dissolved in 100 μL DMSO with gentle shaking for 2 h at room temperature, followed by measuring absorbance at 570 nm in a micro plate reader (Tecan Infinite 200 Pro). Fold change was normalized to control cells (FIG. 12).

Effect of MaP Enzyme Transfection on Human Pancreatic Islet Cultures.

The islets (~200 IEQ) were cultured in six well plates pre-coated with HTB-9 human bladder carcinoma cell matrix prepared as previously described (Jakoby 1978). Each plate was transfected with eukaryotic expression vector (pcDNA3.1) alone or containing RLIP76 or GSTA4 using Lipofectamine 2000 transfection reagent (Invitrogen) following the manufacturer's instructions. After 5 days, the islets were selected by addition of G418 (100 μg/ml) in the medium. The change in morphology of the islets was determined by taking the images every day using phase contrast microscopy (Olympus AX50). The change of morphology at day 20 of the islets is shown at 20× magnification: Controls (FIG. 13A and FIG. 13B), GSTA4 transfected (FIG. 13C and FIG. 13D) and RLIP76-transfected (FIG. 13E and FIG. 13F). After 25 days, the RLIP76-transfected islets were dissociated by trypsinization and grown into precoated six well plates in culture medium containing 11 mM glucose and 100 μg/mL G418. Cell morphology was determined by phase contrast microscopy (FIG. 13G and FIG. 13E, note cell division in FIG. 13G). The expression of RLIP76 was checked in these dissociated cells RT-PCR using two pairs of gene specific primers (see FIG. 13I(A) and FIG. 21 for gene specific primers) and western blot analysis (see FIG. 13I(B), using anti-RLIP76 IgG from Cell Signaling as described (Awasthi 1994).

Effect of RLIP76 Over-Expression on Proliferation of Human Islet Cell In-Vitro.

Human islet cell isolated from human cadaveric pancreas (IRB#11159) were dissociated and placed in cell culture, followed 24 hours later by transient transfection of pcDNA-3 eukaryotic plasmid vector without or with full-length RLIP76. Photomicrographs of cultured cells were taken at 5 days (FIG. 14).

Effect of RLIP76-Liposomes on Proliferation of Human Islet Cells In-Vitro.

Figure 15:
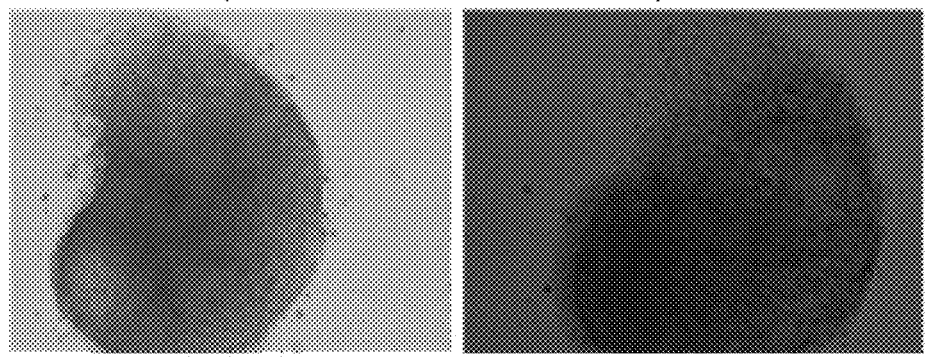
FIG. 15: Effect of RLIP76-liposomes on proliferation of human islet cells in-vitro. Photomicrographs at 20× magnification of human islets isolated from human cadaveric pancreas that treated with RLIP76-liposomes at 40 µg/mL at day 5 and day 10.

Intact human islets isolated from human cadaveric pancreas (IRB#11159) were dissociated and placed in cell culture. The controls were treated with empty liposomes and experimental with RLIP76-liposomes at 40 μg/mL (FIG. 15).

REFERENCES

The references, patents and published patent applications listed below, and all references cited in the specification above are hereby incorporated by reference in their entirety, as if fully set forth herein.

1. Jakoby W B (1978) The glutathione S-transferases: a group of multifunctional detoxification proteins. Adv Enzymol Relat Areas Mol Biol 46:383-414.
2. Awasthi Y C, Sharma R, Singhal S S (1994) Human glutathione S-transferases. Int J Biochem 26:295-308.
3. Sharma R, Yang Y, Sharma A, Awasthi S, Awasthi Y C (2004) Antioxidant role of glutathione S-transferases: protection against oxidant toxicity and regulation of stress-mediated apoptosis. Antioxid Redox Signal 6:289-300.
4. Yang Y, Sharma R, Zimniak P, Awasthi Y C (2002) Role of alpha class glutathione Stransferases as antioxidant enzymes in rodent tissues. Toxicol Appl Pharmacol 182: 105-115.
5. Engle M R, Singh S P, Czernik P J, Gaddy D, Montague D C, Ceci J D, Yang Y, Awasthi S, Awasthi Y C, Zimniak P (2004). Physiological role of mGSTA4-4, a glutathione S-transferase metabolizing 4-hydroxynonenal: generation and studies of mGSTA4 null mouse. Toxicol Appl Pharmacol, 194: 296-308.
6. Awasthi S, Singhal S S, Yadav S, Singhal J, Drake K, Nadkar A, Zajac E, Wickramarachchi D, Rowe N, Yacoub A, Boor P, Dwivedi S, Dent P, Jarman W, John B, Awasthi Y C (2005). RALBP1 is a major determinant of radiation sensitivity. Cancer Res, 65: 6022-6028.
7. Warnke M M, Wanigasekara E, Singhal S S, Singhal J, Awasthi, S, Armstrong D W (2008). The determination of glutathione-4-hydroxynonenal (GS-HNE), E-4-hydroxynonenal (HNE), and E-1-hydroxynon-2-en-4-one (HNO) in mouse liver tissue by LC-ESI-MS. Analyt Bioanal Chem, 392:1325-33.
8. Awasthi S, Singhal S S, Yadav S, Singhal J, Vatsyayan R, Zajac E, Luchowski R, Borvak J, Gryczynski K, Awasthi Y C. (2010). A central role of RLIP76 in regulation of glycemic control. Diabetes, March; 59(3): 714-725.
9. Singhal S S, Wickramarachchi D, Yadav S, Leake K, Vatsyayan R, Lelsani P, Chaudhary P, Suzuki S, Awasthi Y C, Awasthi S (2011a). Glutathione-Conjugate Transport by RLIP76 is required for Clathrin-Dependent Endocytosis and Chemical Carcinogenesis. Mol Cancer Ther, 10(1):16-28.
10. Singhal J, Nagaprashantha L, Vatsyayan R, Awasthi S, Singhal S S (2011b). RLIP76, a glutathione-conjugate transporter, plays a major role in the pathogenesis of metabolic syndrome. PLoS ONE, 6(9): e24688.
11. Singhal S S, Figarola J, Singhal J, Reddy M A, Liu X, Berz D, Natarajan R, Awasthi S (2013). RLIP76 Protein Knockdown Attenuates Obesity Due to a High-fat Diet. J Biol Chem. 288(32):23394-406.

What is claimed is:

1. A method of increasing β-cell viability in a target islet comprising contacting the target islet with a delivery vehicle comprising a molecule comprising a GSTA4 polypeptide having at least 95% sequence identity with an amino acid sequence of SEQ ID NO: 4 or a GSTA4 polynucleotide which encodes the GSTA4 polypeptide, wherein contacting the target islet with the delivery vehicle results in an increase in insulin secretion, thereby increasing β-cell viability.

2. The method of claim 1, wherein contacting the target islet with the delivery vehicle occurs in the media or buffer solution used for isolation, preparation, or storage of the target islet.

3. The method of claim 2, wherein the delivery vehicle is a liposome, nanoparticle, nanotube, non-liposomal lipid, or polymer and comprises the GSTA4 polypeptide.

4. The method of claim 3, wherein the delivery vehicle further comprises a RLIP76 polypeptide having at least 95% sequence identity with an amino acid sequence of SEQ ID NO: 2.

5. The method of claim 2, wherein the delivery vehicle is a plasmid or a viral vector and comprises the GSTA4 polynucleotide, the GSTA4 polynucleotide having at least 95% sequence identity with a DNA sequence of SEQ ID NO: 3.

6. The method of claim 5, wherein the delivery vehicle further comprises a RLIP76 polynucleotide having at least 95% sequence identity with a DNA sequence of SEQ ID NO: 1.

7. The method of claim 6, wherein the delivery vehicle is the viral vector comprising an adenovirus vector, an adeno-associated virus vector, a herpes simplex virus vector, a retrovirus vector, or a lentivirus vector.

* * * * *

SEQUENCE LISTING

```
<160> NUMBER OF SEQ ID NOS: 28

<210> SEQ ID NO 1
<211> LENGTH: 1968
<212> TYPE: DNA
<213> ORGANISM: Homo sapiens

<400> SEQUENCE: 1
atgactgagt gcttcctgcc ccccaccagc agccccagtg aacaccgcag ggtggagcat    60
```

```
ggcagcgggc ttacccggac ccccagctct gaagagatca gccctactaa gtttcctgga    120
ttgtaccgca ctggcgagcc ctcacctccc catgacatcc tccatgagcc tcctgatgta    180
gtgtctgatg atgagaaaga tcatgggaag aaaaaaggga aatttaagaa aaaggaaaag    240
aggactgaag gctatgcagc cttttcaggaa gatagctctg gagatgaggc agaaagtcct   300
tctaaaatga gaggtccaa gggaatccat gttttcaaga agcccagctt ttctaaaaag      360
aaggaaaagg attttaaaat aaaagagaaa cccaaagaag aaaagcataa agaagaaaag    420
cacaaagaag aaaaacataa agagaagaag tcaaaagact tgacagcagc tgatgttgtt    480
aaacagtgga aggaaaagaa gaaaagaaa agccaattc aggagccaga ggtgcctcag       540
attgatgttc caaatctcaa acccattttt ggaattcctt tggctgatgc agtagagagg    600
accatgatgt atgatggcat tcggctgcca gccgttttcc gtgaatgtat agattacgta    660
gagaagtatg gcatgaagtg tgaaggcatc tacagagtat caggaattaa atcaaaggtg    720
gatgagctaa aagcagccta tgaccgggag gagtctacaa acttggaaga ctatgagcct    780
aacactgtag ccagtttgct gaagcagtat ttgcgagacc ttccagagaa tttgcttacc    840
aaagagctta tgcccagatt tgaagaggct tgtgggagga ccacgagac tgagaaagtg      900
caggaattcc agcgtttact caaagaactg ccagaatgta actatcttct gatttcttgg    960
ctcattgtgc acatggacca tgtcattgca aaggaactgg aaacaaaaat gaatatacag   1020
aacatttcta tagtgctcag cccaactgtg cagatcagca atcgagtcct gtatgtgttt   1080
ttcacacatg tgcaagaact ctttggaaat gtggtactaa agcaagtgat gaaacctctg   1140
cgatggtcta acatggccac gatgcccacg ctgccagaga cccaggcggg catcaaggag   1200
gagatcagga gacaggagtt tcttttgaat tgtttacatc gagatctgca gggtgggata   1260
aaggatttgt ctaaagaaga aagattatgg gaagtacaaa gaattttgac agccctcaaa   1320
agaaaactga gagaagctaa aagacaggag tgtgaaacca agattgcaca agagatagcc   1380
agtctttcaa aagaggatgt ttccaaagaa gagatgaatg aaaatgaaga agttataaat   1440
attctccttg ctcaggagaa tgagatcctg actgaacagg aggagctcct ggccatggag   1500
cagtttctgc gccggcagat tgcctcagaa aaagaagaga ttgaacgcct cagagctgag   1560
attgctgaaa ttcagagtcg ccagcagcac ggccgaagtg agactgagga gtactcctcc   1620
gagagcgaga gcgagagtga ggatgaggag gagctgcaga tcattctgga agacttacag   1680
agacagaacg aagagctgga aataaagaac aatcatttga atcaagcaat tcatgaggag   1740
cgcgaggcca tcatcgagct gcgcgtgcag ctgcggctgc tccagatgca gcgagccaag   1800
gccgagcagc aggcgcagga ggacgaggag cctgagtggc gcggggtgc cgtccagccg   1860
cccagagacg cgtccttga gccaaaagca gctaaagagc agccaaaggc aggcaaggag    1920
ccggcaaagc catcgcccag cagggatagg aaggagacgt ccatctga                1968

<210> SEQ ID NO 2
<211> LENGTH: 655
<212> TYPE: PRT
<213> ORGANISM: Homo sapiens

<400> SEQUENCE: 2

Met Thr Glu Cys Phe Leu Pro Pro Thr Ser Pro Ser Glu His Arg
 1               5                  10                  15

Arg Val Glu His Gly Ser Gly Leu Thr Arg Thr Pro Ser Ser Glu Glu
            20                  25                  30
```

```
Ile Ser Pro Thr Lys Phe Pro Gly Leu Tyr Arg Thr Gly Glu Pro Ser
         35                  40                  45

Pro Pro His Asp Ile Leu His Glu Pro Asp Val Val Ser Asp Asp
 50                  55                  60

Glu Lys Asp His Gly Lys Lys Gly Lys Phe Lys Lys Lys Glu Lys
 65                  70                  75                  80

Arg Thr Glu Gly Tyr Ala Ala Phe Gln Glu Asp Ser Ser Gly Asp Glu
                 85                  90                  95

Ala Glu Ser Pro Ser Lys Met Lys Arg Ser Lys Gly Ile His Val Phe
            100                 105                 110

Lys Lys Pro Ser Phe Ser Lys Lys Lys Glu Lys Asp Phe Lys Ile Lys
            115                 120                 125

Glu Lys Pro Lys Glu Glu Lys His Lys Glu Glu Lys His Lys Glu Glu
            130                 135                 140

Lys His Lys Glu Lys Lys Ser Lys Asp Leu Thr Ala Ala Asp Val Val
145                 150                 155                 160

Lys Gln Trp Lys Glu Lys Lys Lys Lys Lys Pro Ile Gln Glu Pro
                 165                 170                 175

Glu Val Pro Gln Ile Asp Val Pro Asn Leu Lys Pro Ile Phe Gly Ile
            180                 185                 190

Pro Leu Ala Asp Ala Val Glu Arg Thr Met Met Tyr Asp Gly Ile Arg
            195                 200                 205

Leu Pro Ala Val Phe Arg Glu Cys Ile Asp Tyr Val Glu Lys Tyr Gly
            210                 215                 220

Met Lys Cys Glu Gly Ile Tyr Arg Val Ser Gly Ile Lys Ser Lys Val
225                 230                 235                 240

Asp Glu Leu Lys Ala Ala Tyr Asp Arg Glu Glu Ser Thr Asn Leu Glu
                245                 250                 255

Asp Tyr Glu Pro Asn Thr Val Ala Ser Leu Leu Lys Gln Tyr Leu Arg
            260                 265                 270

Asp Leu Pro Glu Asn Leu Leu Thr Lys Glu Leu Met Pro Arg Phe Glu
            275                 280                 285

Glu Ala Cys Gly Arg Thr Thr Glu Thr Glu Lys Val Gln Glu Phe Gln
            290                 295                 300

Arg Leu Leu Lys Glu Leu Pro Glu Cys Asn Tyr Leu Leu Ile Ser Trp
305                 310                 315                 320

Leu Ile Val His Met Asp His Val Ile Ala Lys Glu Leu Glu Thr Lys
                325                 330                 335

Met Asn Ile Gln Asn Ile Ser Ile Val Leu Ser Pro Thr Val Gln Ile
            340                 345                 350

Ser Asn Arg Val Leu Tyr Val Phe Phe Thr His Val Gln Glu Leu Phe
            355                 360                 365

Gly Asn Val Val Leu Lys Gln Val Met Lys Pro Leu Arg Trp Ser Asn
            370                 375                 380

Met Ala Thr Met Pro Thr Leu Pro Glu Thr Gln Ala Gly Ile Lys Glu
385                 390                 395                 400

Glu Ile Arg Arg Gln Glu Phe Leu Leu Asn Cys Leu His Arg Asp Leu
                405                 410                 415

Gln Gly Gly Ile Lys Asp Leu Ser Lys Glu Glu Arg Leu Trp Glu Val
            420                 425                 430

Gln Arg Ile Leu Thr Ala Leu Lys Arg Lys Leu Arg Glu Ala Lys Arg
            435                 440                 445

Gln Glu Cys Glu Thr Lys Ile Ala Gln Glu Ile Ala Ser Leu Ser Lys
```

```
                450             455             460
Glu Asp Val Ser Lys Glu Glu Met Asn Glu Asn Glu Val Ile Asn
465                 470                 475                 480

Ile Leu Leu Ala Gln Glu Asn Glu Ile Leu Thr Gln Gln Glu Leu
                485                 490                 495

Leu Ala Met Glu Gln Phe Leu Arg Arg Gln Ile Ala Ser Glu Lys Glu
                500                 505                 510

Glu Ile Glu Arg Leu Arg Ala Glu Ile Ala Glu Ile Gln Ser Arg Gln
                515                 520                 525

Gln His Gly Arg Ser Glu Thr Glu Glu Tyr Ser Ser Glu Ser Glu Ser
                530                 535                 540

Glu Ser Glu Asp Glu Glu Leu Gln Ile Ile Leu Glu Asp Leu Gln
545                 550                 555                 560

Arg Gln Asn Glu Glu Leu Glu Ile Lys Asn Asn His Leu Asn Gln Ala
                565                 570                 575

Ile His Glu Glu Arg Glu Ala Ile Ile Glu Leu Arg Val Gln Leu Arg
                580                 585                 590

Leu Leu Gln Met Gln Arg Ala Lys Ala Glu Gln Gln Ala Gln Glu Asp
                595                 600                 605

Glu Glu Pro Glu Trp Arg Gly Gly Ala Val Gln Pro Arg Asp Gly
610                 615                 620

Val Leu Glu Pro Lys Ala Ala Lys Glu Gln Pro Lys Ala Gly Lys Glu
625                 630                 635                 640

Pro Ala Lys Pro Ser Pro Ser Arg Asp Arg Lys Glu Thr Ser Ile
                645                 650                 655

<210> SEQ ID NO 3
<211> LENGTH: 669
<212> TYPE: DNA
<213> ORGANISM: Homo sapiens

<400> SEQUENCE: 3
atggcagcaa ggcccaagct ccactatccc aacggaagag gccggatgga gtccgtgaga      60
tgggttttag ctgccgccgg agtcgagttt gatgaagaat ttctggaaac aaaagaacag     120
ttgtacaagt tgcaggatgg taaccacctg ctgttccaac aagtgcccat ggttgaaatt     180
gacgggatga gttggtaca gacccgaagc attctccact acatagcaga caagcacaat      240
ctctttggca agaacctcaa ggagagaacc ctgattgaca tgtacgtgga ggggacactg     300
gatctgctgg aactgcttat catgcatcct ttcttaaaac cagatgatca gcaaaaggaa     360
gtggttaaca tggcccagaa ggctataatt agatactttc ctgtgtttga aaagatttta     420
aggggtcacg gacaaagctt tcttgttggt aatcagctga ccttgcaga tgtgatttta      480 ctccaaacca ttttagctct agaagagaaa attcctaata tcctgtctgc atttcctttc     540
ctccaggaat acacagtgaa actaagtaat atccctacaa ttaagagatt ccttgaacct     600
ggcagcaaga agaagcctcc ccctgatgaa atttatgtga gaaccgtcta caacatcttt     660
aggccataa                                                             669

<210> SEQ ID NO 4
<211> LENGTH: 222
<212> TYPE: PRT
<213> ORGANISM: Homo sapiens

<400> SEQUENCE: 4

Met Ala Ala Arg Pro Lys Leu His Tyr Pro Asn Gly Arg Gly Arg Met
```

|  |  |  |  |
|---|---|---|---|
| 1 | 5 | 10 | 15 |

Glu Ser Val Arg Trp Val Leu Ala Ala Ala Gly Val Glu Phe Asp Glu
             20                   25                   30

Glu Phe Leu Glu Thr Lys Glu Gln Leu Tyr Lys Leu Gln Asp Gly Asn
             35                   40                   45

His Leu Leu Phe Gln Gln Val Pro Met Val Glu Ile Asp Gly Met Lys
 50                       55                   60

Leu Val Gln Thr Arg Ser Ile Leu His Tyr Ile Ala Asp Lys His Asn
65                   70                   75                   80

Leu Phe Gly Lys Asn Leu Lys Glu Arg Thr Leu Ile Asp Met Tyr Val
             85                   90                   95

Glu Gly Thr Leu Asp Leu Leu Glu Leu Leu Ile Met His Pro Phe Leu
            100                105               110

Lys Pro Asp Asp Gln Gln Lys Glu Val Val Asn Met Ala Gln Lys Ala
            115                120               125

Ile Ile Arg Tyr Phe Pro Val Phe Glu Lys Ile Leu Arg Gly His Gly
            130                135               140

Gln Ser Phe Leu Val Gly Asn Gln Leu Ser Leu Ala Asp Val Ile Leu
145                 150                155               160

Leu Gln Thr Ile Leu Ala Leu Glu Glu Lys Ile Pro Asn Ile Leu Ser
            165                170               175

Ala Phe Pro Phe Leu Gln Glu Tyr Thr Val Lys Leu Ser Asn Ile Pro
            180                185               190

Thr Ile Lys Arg Phe Leu Glu Pro Gly Ser Lys Lys Lys Pro Pro Pro
            195                200               205

Asp Glu Ile Tyr Val Arg Thr Val Tyr Asn Ile Phe Arg Pro
210                 215                220

<210> SEQ ID NO 5
<211> LENGTH: 4368
<212> TYPE: DNA
<213> ORGANISM: Homo sapiens

<400> SEQUENCE: 5

```
atcattgtaa acaggcagag gctgggcggg gtgggaatgg ggcgcccgag gccggcctgg      60
ggcgcagcgc aggaggcggc tccggtggct gcggcggcag cgtgagcgcg aggaggcgga     120
ggctgcggcg gggcggacgg tcgcgcggcg gcaggcacag gtgtaatgga taggtaacag     180
agaagacctc gtcccttcct agtcagggca tcagcatgac tgagtgcttc ctgcccccca     240
ccagcagccc cagtgaacac cgcagggtgg agcatggcag cgggcttacc cggacccccg     300
gctctgaaga gatcagccct actaagtttc ctggattgta ccgcactggc gagccctcac     360
ctccccatga catcctccat gagcctcctg atgtagtgtc tgatgatgag aaagatcatg     420
ggaagaaaaa agggaaattt aagaaaaagg aaaagaggac tgaaggctat gcagcctttc     480
aggaagatag ctctggagat gaggcagaaa gtccttctaa aatgaagagg tccaagggaa     540
tccatgtttt caagaagccc agcttttcta aaaagaagga aaaggatttt aaaataaaag     600
agaaacccaa agaagaaaag cataagaaag aaaagcacaa agaagaaaaa cataagagaa     660
agaagtcaaa agacttgaca gcagctgatg ttgttaaaca gtggaaggaa aagaagaaaa     720
agaaaaagcc aattcaggag ccagaggtgc ctcagattga tgttccaaat ctcaaaccca     780
tttttggaat cctttggct gatgcagtag agaggaccat gatgtatgat ggcattcggc     840
tgccagccgt tttccgtgaa tgtatagatt acgtagagaa gtatggcatg aagtgtgaag     900
```

```
gcatctacag agtatcagga attaaatcaa aggtggatga gctaaaagca gcctatgacc    960
gggaggagtc tacaaacttg gaagactatg agcctaacac tgtagccagt ttgctgaagc   1020
agtatttgcg agaccttcca gagaatttgc ttaccaaaga gcttatgccc agatttgaag   1080
aggcttgtgg gaggaccacg gagactgaga aagtgcagga attccagcgt ttactcaaag   1140
aactgccaga atgtaactat cttctgattt cttggctcat tgtgcacatg gaccatgtca   1200
ttgcaaagga actggaaaca aaaatgaata tacagaacat ttctatagtg ctcagcccaa   1260
ctgtgcagat cagcaatcga gtcctgtatg tgtttttcac acatgtgcaa gaactctttg   1320
gaaatgtggt actaaagcaa gtgatgaaac ctctgcgatg gtctaacatg ccacgatgc    1380 ccacgctgcc agagacccag gcgggcatca aggaggagat caggagacag gagtttcttt   1440
tgaattgttt acatcgagat ctgcagggtg ggataaagga tttgtctaaa gaagaaagat   1500
tatgggaagt acaagaatt ttgacagccc tcaaaagaaa actgagagaa gctaaaagac    1560
aggagtgtga aaccaagatt gcacaagaga tagccagtct ttcaaaagag gatgtttcca   1620
aagaagagat gaatgaaaat gaagaagtta taaatattct ccttgctcag gagaatgaga   1680
tcctgactga acaggaggag ctcctggcca tggagcagtt tctgcgccgg cagattgcct   1740
cagaaaaaga agagattgaa cgcctcagag ctgagattgc tgaaattcag agtcgccagc   1800
agcacggccg aagtgagact gaggagtact cctccgagag cgagagcgag agtgaggatg   1860
aggaggagct gcagatcatt ctggaagact acagagaca gaacgaagag ctggaaataa    1920
agaacaatca tttgaatcaa gcaattcatg aggagcgcga ggccatcatc gagctgcgcg   1980
tgcagctgcg gctgctccag atgcagcgag ccaaggccga gcagcaggcg caggaggacg   2040
aggagcctga gtggcgcggg ggtgccgtcc agccgcccag agacggcgtc cttgagccaa   2100
aagcagctaa agagcagcca aaggcaggca aggagcggc aaagccatcg cccagcaggg    2160
ataggaagga gacgtccatc tgagcagcct gcgtggccgt ctggagtccg tgagactgaa   2220
aggacccgtg catcttactg taacccgggg gccaggccgg ctctctcgct gtacattctg   2280
taaaggtgtc ttctcttctc agactcttcc tctgtcacac gtctgactcc ttcacgtcag   2340
gctcaggttc catgggagga cgaagcagtg gacgcattgt gggctttagg acagatgag    2400 ttttccagat agtgtcagct tatttgaaga ttaattttct ttgttaactt aaaataacta   2460
ttttaaccct tgagtggctt ctttttaaac caaaaccgt cttttctttgc ttttttatca    2520 cagcagaatc aggatctctt tctcattcaa gggggaacc accccaggtc agcgctgcgc    2580
ctgctgtggc cgccgcgagc cacgccctct gggatctctg gtaccgtcac tcttgcttgt   2640
gccttccaca ccttctcggt gcagatccct atggggagc tgcctcacgt tctctgactg    2700
gtcagagcag cgcctggtgg gtgttccctg gcccactctc ctctctcctt ctgcagttct   2760
aaaccacagt ctataagccc gagtcaccag gacggcctgt ctggccacag acaggggctg   2820
cctgtggagc ctgcccaccg gccccggca gtgcagtcca gcggggagga ggctgccccgt   2880 tcctgccagt tcctcactgc ggggaccagc aaaggccttc tcactgggtt ggtcaaaggt   2940
agtcaccttg gcctggtgca tccacagagg atgttgttca aaccagaaat cttttaaacg   3000
actgaccttc cttaaaaaca gaatgactcc gattgcttgc ttgggctaga atgtacacgt   3060
ctccttgcct gaataagcca tatatatgct cttaaacaaa agtttgaaat tatccatatc   3120
atctcagtga acctactggt ggactcccaa ttgacaagat tgagcaatag aaaaaaattc   3180
ctttcctttg aatgatagct gtgattcacc ccacccatt ttcttgtttc tggtccatcc    3240
gatgagacgg atgctctgat gctctgaggc ttctgggagg ctgggccctg gaggcaacgt   3300
```

```
gctgcaggcg cactctgtca gagtgaacag caccgcgaga caggccaggc tcgtggctcg    3360
gaagacaaac cccacacaca ctcaagggt cgaaaacaaa ccccacacga gggctctcac    3420
ctccttctcc taggtagtat ttattttcag cacctgtttg atgcagtttt taatcctcta    3480
cctattgcac tgttgtgact cgttggccat tatttgattt ttgtacgaaa aaaagctttg    3540
ttatagaaat cagcatacta ttttttttaaa tctggagaga agatattctg gtgactgaaa    3600
gtatggtcgg gtgtcagata taaatgtgca aatgccttct tgctgtcctg tcggtctcag    3660
tacgttcact ttatagctgc tggcaatatc gaaggttcct ttttgtttg tgtaaactct    3720 aatttctatc aaggtgtcat ggatttttaa aattagtatt tcattacaaa tgtctcagca    3780
ttggttaact aattttttgcc aggaccatta ttgatcaagc aaataaattc aacagccatt    3840
tgggaaaaag aaaagcttct agttttttg tacacattct ttctgtgagg agattgagta    3900
ctctgcagct ggcgaggagt tggttgaggc acttcttcaa ggccaagggg gaacacagtg    3960
ttttgtttcc agctcacttt gtaccctca cctctgcaga cacggggaga accccggacc    4020
cctggcatgc atgctggcgg cggcatgcct cccttccaca agcccatgct gctgcagagg    4080
gagcctgtgt ttgcaaaacc cagtggactg ggctgggtct gctgtctgag cagctcctgg    4140
ctccggtggg aactgcacac aagtccactg gcctggcttg gccccaggca ttgcaattga    4200
cagacatttg catttcatac ggtaaatgag gactcagcac agccaaccat aatcagcatg    4260
tctgggatag actggtctag aataaaaatg aagtttccat tgctttgttt gctttaaaaa    4320
ttccacaatt aaaatatctg tcattgaaag cttaaaaaaa aaaaaaa              4368

<210> SEQ ID NO 6
<211> LENGTH: 21
<212> TYPE: DNA
<213> ORGANISM: Artificial Sequence
<220> FEATURE:
<223> OTHER INFORMATION: GSTA4 forward primer

<400> SEQUENCE: 6
caggagtcat ggaagtcaaa c                                               21

<210> SEQ ID NO 7
<211> LENGTH: 23
<212> TYPE: DNA
<213> ORGANISM: Artificial Sequence
<220> FEATURE:
<223> OTHER INFORMATION: GSTA4 reverse primer

<400> SEQUENCE: 7
ttctcatatt gttctctcgt ctc                                             23

<210> SEQ ID NO 8
<211> LENGTH: 20
<212> TYPE: DNA
<213> ORGANISM: Artificial Sequence
<220> FEATURE:
<223> OTHER INFORMATION: RLIP76 forward primer

<400> SEQUENCE: 8
ttcaagaagc ccagcttttc                                                 20

<210> SEQ ID NO 9
<211> LENGTH: 20
<212> TYPE: DNA
<213> ORGANISM: Artificial Sequence
<220> FEATURE:
```

<223> OTHER INFORMATION: RLIP76 reverse primer

<400> SEQUENCE: 9
attctctgga aggtctcgca                                               20

<210> SEQ ID NO 10
<211> LENGTH: 20
<212> TYPE: DNA
<213> ORGANISM: Artificial Sequence
<220> FEATURE:
<223> OTHER INFORMATION: beta-actin forward primer

<400> SEQUENCE: 10
cacccgcgac tacaaccttc                                               20

<210> SEQ ID NO 11
<211> LENGTH: 20
<212> TYPE: DNA
<213> ORGANISM: Artificial Sequence
<220> FEATURE:
<223> OTHER INFORMATION: beta-actin reverse primer

<400> SEQUENCE: 11
cccataccca ccatcacacc                                               20

<210> SEQ ID NO 12
<211> LENGTH: 22
<212> TYPE: DNA
<213> ORGANISM: Artificial Sequence
<220> FEATURE:
<223> OTHER INFORMATION: insulin-1 forward primer

<400> SEQUENCE: 12
tagtgaccag ctataatcag ag                                            22

<210> SEQ ID NO 13
<211> LENGTH: 20
<212> TYPE: DNA
<213> ORGANISM: Artificial Sequence
<220> FEATURE:
<223> OTHER INFORMATION: insulin-1 reverse primer

<400> SEQUENCE: 13
acgccaaggt ctgaaggtcc                                               20

<210> SEQ ID NO 14
<211> LENGTH: 19
<212> TYPE: DNA
<213> ORGANISM: Artificial Sequence
<220> FEATURE:
<223> OTHER INFORMATION: insulin-2 forward primer

<400> SEQUENCE: 14
ccctgctggc cctgctctt                                                19

<210> SEQ ID NO 15
<211> LENGTH: 20
<212> TYPE: DNA
<213> ORGANISM: Artificial Sequence
<220> FEATURE:
<223> OTHER INFORMATION: insulin-2 reverse primer

<400> SEQUENCE: 15
aggtctgaag gtcacctgct                                               20

```
<210> SEQ ID NO 16
<211> LENGTH: 27
<212> TYPE: DNA
<213> ORGANISM: Artificial Sequence
<220> FEATURE:
<223> OTHER INFORMATION: glucagon forward primer

<400> SEQUENCE: 16
gaattcattg cttggctggt gaaaggc                                          27

<210> SEQ ID NO 17
<211> LENGTH: 27
<212> TYPE: DNA
<213> ORGANISM: Artificial Sequence
<220> FEATURE:
<223> OTHER INFORMATION: glucagon reverse primer

<400> SEQUENCE: 17
catttcaaac atcccacgtg gcatgca                                          27

<210> SEQ ID NO 18
<211> LENGTH: 24
<212> TYPE: DNA
<213> ORGANISM: Artificial Sequence
<220> FEATURE:
<223> OTHER INFORMATION: NgN3 forward primer

<400> SEQUENCE: 18
ctgcgcatag cggaccacag cttc                                             24

<210> SEQ ID NO 19
<211> LENGTH: 23
<212> TYPE: DNA
<213> ORGANISM: Artificial Sequence
<220> FEATURE:
<223> OTHER INFORMATION: NgN3 reverse primer

<400> SEQUENCE: 19
cacaagaagt ctgagaacac cag                                              23

<210> SEQ ID NO 20
<211> LENGTH: 20
<212> TYPE: DNA
<213> ORGANISM: Artificial Sequence
<220> FEATURE:
<223> OTHER INFORMATION: PDX1 forward primer

<400> SEQUENCE: 20
ccaccccagt ttacaagctc                                                  20

<210> SEQ ID NO 21
<211> LENGTH: 20
<212> TYPE: DNA
<213> ORGANISM: Artificial Sequence
<220> FEATURE:
<223> OTHER INFORMATION: PDX1 reverse primer

<400> SEQUENCE: 21
tgtaggcagt acgggtcctc                                                  20

<210> SEQ ID NO 22
<211> LENGTH: 20
<212> TYPE: DNA
<213> ORGANISM: Artificial Sequence
<220> FEATURE:
<223> OTHER INFORMATION: TNF-alpha forward primer
```

```
<400> SEQUENCE: 22
tgttgcctcc tcttttgctt                                              20

<210> SEQ ID NO 23
<211> LENGTH: 20
<212> TYPE: DNA
<213> ORGANISM: Artificial Sequence
<220> FEATURE:
<223> OTHER INFORMATION: TNF-alpha reverse primer

<400> SEQUENCE: 23
tggtcaccaa atcagcgtta                                              20

<210> SEQ ID NO 24
<211> LENGTH: 22
<212> TYPE: DNA
<213> ORGANISM: Artificial Sequence
<220> FEATURE:
<223> OTHER INFORMATION: IL-6 forward primer

<400> SEQUENCE: 24
acaaagccag agtccttcag ag                                           22

<210> SEQ ID NO 25
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 25
accacagtga ggaatgtcca c                                            21

<210> SEQ ID NO 26
<211> LENGTH: 21
<212> TYPE: DNA
<213> ORGANISM: Artificial Sequence
<220> FEATURE:
<223> OTHER INFORMATION: MCP-1 forward primer

<400> SEQUENCE: 26
aggtccctgt catgcttctg g                                            21

<210> SEQ ID NO 27
<211> LENGTH: 25
<212> TYPE: DNA
<213> ORGANISM: Artificial Sequence
<220> FEATURE:
<223> OTHER INFORMATION: MCP-1 reverse primer

<400> SEQUENCE: 27
cagcacttct ttgggacacc tgctg                                        25

<210> SEQ ID NO 28
<211> LENGTH: 23
<212> TYPE: DNA
<213> ORGANISM: Artificial Sequence
<220> FEATURE:
<223> OTHER INFORMATION: RLIP76 reverse primer (497 bp size band)

<400> SEQUENCE: 28
tcaaaagaaa ctcctgtctc ctg                                          23
```